United States Patent
Foley et al.

(10) Patent No.: US 6,501,973 B1
(45) Date of Patent: Dec. 31, 2002

(54) APPARATUS AND METHOD FOR MEASURING SELECTED PHYSICAL CONDITION OF AN ANIMATE SUBJECT

(75) Inventors: Barbara M. Foley, Gilbert, AZ (US); Gary W. Grube, Barrington, IL (US)

(73) Assignee: Motorola, Inc., Schaumburg, IL (US)

( * ) Notice: Subject to any disclaimer, the term of this patent is extended or adjusted under 35 U.S.C. 154(b) by 31 days.

(21) Appl. No.: 09/607,722

(22) Filed: Jun. 30, 2000

(51) Int. Cl.[7] ................................. A61B 5/00
(52) U.S. Cl. ...................................... 600/310
(58) Field of Search ................. 600/310, 316, 600/322, 323, 473, 476; 356/39, 40, 41

(56) References Cited

U.S. PATENT DOCUMENTS

| | | |
|---|---|---|
| 3,670,213 A | 6/1972 | Nakawaga et al. |
| 3,802,967 A | 4/1974 | Ladany et al. |
| 4,006,989 A | 2/1977 | Andringa |
| 4,174,422 A | 11/1979 | Matthews et al. |
| 4,242,595 A | 12/1980 | Lehovec |
| 4,284,329 A | 8/1981 | Smith et al. |
| 4,398,342 A | 8/1983 | Pitt et al. |
| 4,404,265 A | 9/1983 | Manasevit |
| 4,482,422 A | 11/1984 | McGinn et al. |
| 4,482,906 A | 11/1984 | Hovel et al. |
| 4,484,332 A | 11/1984 | Hawrylo |
| 4,523,211 A | 6/1985 | Morimoto et al. |
| 4,661,176 A | 4/1987 | Manasevit |

(List continued on next page.)

FOREIGN PATENT DOCUMENTS

| | | |
|---|---|---|
| DE | 197 12 496 | 10/1997 |
| EP | 0 250 171 | 12/1987 |
| EP | 0 342937 | 11/1989 |
| EP | 0 455 526 | 6/1991 |

(List continued on next page.)

OTHER PUBLICATIONS

Nakagawara et al., Effects of Buffer Layers in Epitaxial Growth of $SrTiO_3$ Thin Film on Si(100), *J. Appl. Phys.*, 78 (12), Dec. 15, 1995, pp. 7226–7230.

Suzuki et al., "A Proposal of Epitaxial Oxide Thin Film Structures For Future Oxide Electronics", *Materials Science and Engineering B41*, (1996), pp. 166–173.

(List continued on next page.)

*Primary Examiner*—Eric F. Winakur
(74) *Attorney, Agent, or Firm*—Oblon, Spivak, McClelland, Maier & Neustadt, P.C.

(57) ABSTRACT

An apparatus for measuring at least one selected physical condition of an animate subject is disclosed. The apparatus comprises: (a) a light source; (b) a light receiver that receives resultant light from the light source via the subject; and (c) an information processor connected with the light receiver. The processor receives indication of the resultant light from the light receiver and evaluates the indication to effect the measuring. The processor is implemented in a unitary structure with the light source and light detector that is borne upon a single silicon substrate. The apparatus may further comprise a first interface element coupled with the processor to facilitate communication with the light receiver, and a second interface element coupled with the processor that includes communication means for conveying messages to remote loci. The first and second interface elements are implemented in the unitary structure. The method of the present invention comprises the steps of: (a) providing an apparatus implemented in a unitary structure borne upon a single silicon substrate; and (b) evaluating the indication provided by the apparatus to effect the measuring. The unitary structure is comprised of a monolithic structure having a first portion implemented in silicon, and having a second portion implemented in at least one compound semiconductor material.

39 Claims, 12 Drawing Sheets

U.S. PATENT DOCUMENTS

| | | |
|---|---|---|
| 4,667,088 A | 5/1987 | Kramer |
| 4,756,007 A | 7/1988 | Qureshi et al. |
| 4,772,929 A | 9/1988 | Manchester et al. |
| 4,773,063 A | 9/1988 | Hunsperger et al. |
| 4,793,872 A | 12/1988 | Meunier et al. |
| 4,802,182 A | 1/1989 | Thornton et al. |
| 4,815,084 A | 3/1989 | Scifres et al. |
| 4,841,775 A | 6/1989 | Ikeda et al. |
| 4,845,044 A | 7/1989 | Ariyoshi et al. |
| 4,846,926 A | 7/1989 | Kay et al. |
| 4,855,249 A | 8/1989 | Akasaki et al. |
| 4,868,376 A | 9/1989 | Lessin et al. |
| 4,876,219 A | 10/1989 | Eshita et al. |
| 4,882,300 A | 11/1989 | Inoue et al. |
| 4,891,091 A | 1/1990 | Shastry |
| 4,896,194 A | 1/1990 | Suzuki |
| 4,912,087 A | 3/1990 | Aslam et al. |
| 4,928,154 A | 5/1990 | Umeno et al. |
| 4,963,508 A | 10/1990 | Umeno et al. |
| 4,963,949 A | 10/1990 | Wanlass et al. |
| 4,999,842 A | 3/1991 | Huang et al. |
| 5,051,790 A | 9/1991 | Hammer |
| 5,055,445 A | 10/1991 | Belt et al. |
| 5,060,031 A | 10/1991 | Abrokwah et al. |
| 5,063,166 A | 11/1991 | Mooney et al. |
| 5,081,062 A | 1/1992 | Vasudev et al. |
| 5,081,519 A | 1/1992 | Nishimura et al. |
| 5,116,461 A | 5/1992 | Lebby et al. |
| 5,127,067 A | 6/1992 | Delcoco et al. |
| 5,141,894 A | 8/1992 | Bisaro et al. |
| 5,144,409 A | 9/1992 | Ma |
| 5,155,658 A | 10/1992 | Inam et al. |
| 5,159,413 A | 10/1992 | Calviello et al. |
| 5,173,474 A | 12/1992 | Connell et al. |
| 5,185,589 A | 2/1993 | Krishnaswamy et al. |
| 5,191,625 A | 3/1993 | Gustavsson |
| 5,194,397 A | 3/1993 | Cook et al. |
| 5,221,367 A | 6/1993 | Chisholm et al. |
| 5,225,031 A | 7/1993 | McKee et al. |
| 5,248,564 A | 9/1993 | Ramesh |
| 5,270,298 A | 12/1993 | Ramesh |
| 5,286,985 A | 2/1994 | Taddiken |
| 5,293,050 A | 3/1994 | Chapple-Sokol et al. |
| 5,310,707 A | 5/1994 | Oishi et al. |
| 5,314,547 A | 5/1994 | Heremans et al. |
| 5,326,721 A | 7/1994 | Summerfelt |
| 5,352,926 A | 10/1994 | Andrews |
| 5,356,509 A | 10/1994 | Terranova et al. |
| 5,356,831 A | 10/1994 | Calviello et al. |
| 5,358,925 A | 10/1994 | Connell et al. |
| 5,371,734 A | 12/1994 | Fischer |
| 5,391,515 A | 2/1995 | Kao et al. |
| 5,393,352 A | 2/1995 | Summerfelt |
| 5,394,489 A | 2/1995 | Koch |
| 5,404,581 A | 4/1995 | Honjo |
| 5,405,802 A | 4/1995 | Yamagata et al. |
| 5,406,202 A | 4/1995 | Mehrgardt et al. |
| 5,418,216 A | 5/1995 | Fork |
| 5,418,389 A | 5/1995 | Watanabe |
| 5,436,759 A | 7/1995 | Dijaii et al. |
| 5,442,191 A | 8/1995 | Ma |
| 5,442,561 A | 8/1995 | Yoshizawa et al. |
| 5,444,016 A | 8/1995 | Abrokwah et al. |
| 5,450,812 A | 9/1995 | McKee et al. |
| 5,453,727 A | 9/1995 | Shibasaki et al. |
| 5,466,631 A | 11/1995 | Ichikawa et al. |
| 5,473,047 A | 12/1995 | Shi |
| 5,478,653 A | 12/1995 | Guenzer |
| 5,480,829 A | 1/1996 | Abrokwah et al. |
| 5,482,003 A | 1/1996 | McKee et al. |
| 5,486,406 A | 1/1996 | Shi |
| 5,491,461 A | 2/1996 | Partin et al. |
| 5,492,859 A | 2/1996 | Sakaguchi et al. |
| 5,494,711 A | 2/1996 | Takeda et al. |
| 5,504,035 A | 4/1996 | Rostoker et al. |
| 5,504,183 A | 4/1996 | Shi |
| 5,511,238 A | 4/1996 | Bayraktaroglu |
| 5,514,484 A | 5/1996 | Nashimoto |
| 5,515,047 A | 5/1996 | Yamakido et al. |
| 5,515,810 A | 5/1996 | Yamashita et al. |
| 5,519,235 A | 5/1996 | Ramesh |
| 5,528,067 A | 6/1996 | Farb et al. |
| 5,528,414 A | 6/1996 | Oakley |
| 5,549,977 A | 8/1996 | Jin et al. |
| 5,552,547 A | 9/1996 | Shi |
| 5,556,463 A | 9/1996 | Guenzer |
| 5,572,052 A | 11/1996 | Kashihara et al. |
| 5,576,879 A | 11/1996 | Nashimoto |
| 5,588,995 A | 12/1996 | Sheldon |
| 5,602,418 A | 2/1997 | Imai et al. |
| 5,606,184 A | 2/1997 | Abrokwah et al. |
| 5,614,739 A | 3/1997 | Abrokwah et al. |
| 5,640,267 A | 6/1997 | May et al. |
| 5,659,180 A | 8/1997 | Shen et al. |
| 5,670,798 A | 9/1997 | Schetzina |
| 5,674,366 A | 10/1997 | Hayashi et al. |
| 5,679,965 A | 10/1997 | Schetzina |
| 5,729,394 A | 3/1998 | Sevier et al. |
| 5,729,641 A | 3/1998 | Chandonnet et al. |
| 5,731,220 A | 3/1998 | Tsu et al. |
| 5,733,641 A | 3/1998 | Fork et al. |
| 5,735,949 A | 4/1998 | Mantl et al. |
| 5,741,724 A | 4/1998 | Ramdani et al. |
| 5,764,676 A | 6/1998 | Paoli et al. |
| 5,777,350 A | 7/1998 | Nakamura et al. |
| 5,777,762 A | 7/1998 | Yamamoto |
| 5,778,018 A | 7/1998 | Yoshikawa et al. |
| 5,778,116 A | 7/1998 | Tomich |
| 5,789,845 A | 8/1998 | Wadaka et al. |
| 5,790,583 A | 8/1998 | Ho |
| 5,792,679 A | 8/1998 | Nakato |
| 5,801,072 A | 9/1998 | Barber |
| 5,801,105 A | 9/1998 | Yano et al. |
| 5,810,923 A | 9/1998 | Yano et al. |
| 4,777,613 A | 10/1998 | Shahan et al. |
| 5,825,055 A | 10/1998 | Summerfelt |
| 5,825,799 A | 10/1998 | Ho et al. |
| 5,827,755 A | 10/1998 | Yonchara et al. |
| 5,828,080 A | 10/1998 | Yano et al. |
| 5,830,270 A | 11/1998 | McKee et al. |
| 5,833,603 A * | 11/1998 | Kovacs et al. .......... 600/317 |
| 5,838,035 A | 11/1998 | Ramesh |
| 5,846,846 A | 12/1998 | Suh et al. |
| 5,857,049 A | 1/1999 | Beranek et al. |
| 5,858,814 A | 1/1999 | Goossen et al. |
| 5,861,966 A | 1/1999 | Ortel |
| 5,863,326 A | 1/1999 | Nause et al. |
| 5,874,860 A | 2/1999 | Brunel et al. |
| 5,880,452 A | 3/1999 | Plesko |
| 5,883,564 A | 3/1999 | Partin |
| 5,883,996 A | 3/1999 | Knapp et al. |
| 5,907,792 A | 5/1999 | Droopad et al. |
| 5,912,068 A | 6/1999 | Jia |
| 5,926,496 A | 7/1999 | Ho et al. |
| 5,937,274 A | 8/1999 | Kondow et al. |
| 5,937,285 A | 8/1999 | Abrokwah et al. |
| 5,981,400 A | 11/1999 | Lo |
| 5,987,011 A | 11/1999 | Toh |
| 5,990,495 A | 11/1999 | Ohba |
| 5,995,359 A | 11/1999 | Klee et al. |
| 6,002,375 A | 12/1999 | Corman et al. |

| | | |
|---|---|---|
| 6,008,762 A | 12/1999 | Nohiem |
| 6,020,222 A | 2/2000 | Wollesen |
| 6,022,140 A | 2/2000 | Fraden et al. |
| 6,023,082 A | 2/2000 | McKee et al. |
| 6,028,853 A | 2/2000 | Haartsen |
| 6,045,626 A | 4/2000 | Yano et al. |
| 6,049,702 A | 4/2000 | Tham et al. |
| 6,055,179 A | 4/2000 | Koganei et al. |
| 6,058,131 A | 5/2000 | Pan |
| 6,064,078 A | 5/2000 | Northrup et al. |
| 6,064,092 A | 5/2000 | Park |
| 6,078,717 A | 6/2000 | Nashimoto et al. |
| 6,096,584 A | 8/2000 | Ellis-Monaghan et al. |
| 6,103,008 A | 8/2000 | McKee et al. |
| 6,107,653 A | 8/2000 | Fitzgerald |
| 6,113,690 A | 9/2000 | Yu et al. |
| 6,114,996 A | 9/2000 | Nghiem |
| 6,121,642 A | 9/2000 | Newns |
| 6,128,178 A | 10/2000 | Newns |
| 6,136,666 A | 10/2000 | So |
| 6,137,603 A | 10/2000 | Henmi |
| 6,143,072 A | 11/2000 | McKee et al. |
| 6,146,906 A | 11/2000 | Inoue et al. |
| 6,153,010 A | 11/2000 | Kiyoku et al. |
| 6,153,454 A | 11/2000 | Krivokapic |
| 6,173,474 B1 | 1/2001 | Conrad |
| 6,174,755 B1 | 1/2001 | Manning |
| 6,175,497 B1 | 1/2001 | Tseng et al. |
| 6,180,252 B1 | 1/2001 | Farrell et al. |
| 6,180,486 B1 | 1/2001 | Leobandung et al. |
| 6,184,044 B1 | 2/2001 | Sone et al. |
| 6,184,144 B1 | 2/2001 | Lo |
| 6,191,011 B1 | 2/2001 | Gilboa et al. |
| 6,204,737 B1 | 3/2001 | Ella |
| 6,222,654 B1 | 4/2001 | Frigo |
| 6,224,669 B1 | 5/2001 | Yi et al. |
| 6,241,821 B1 | 6/2001 | Yu et al. |
| 6,248,459 B1 | 6/2001 | Wang et al. |
| 6,252,261 B1 | 6/2001 | Usui et al. |
| 6,255,198 B1 | 7/2001 | Linthicum et al. |
| 6,268,269 B1 | 7/2001 | Lee et al. |
| 6,291,319 B1 | 9/2001 | Yu et al. |
| 6,316,785 B1 | 11/2001 | Nunoue et al. |
| 6,316,832 B1 | 11/2001 | Tsuzuki et al. |
| 6,343,171 B1 | 1/2002 | Yoshimura et al. |
| 2001/0013313 A1 | 8/2001 | Droopad et al. |

FOREIGN PATENT DOCUMENTS

| | | |
|---|---|---|
| EP | 0 514 018 | 11/1992 |
| EP | 0 581 239 | 2/1994 |
| EP | 0 602 568 | 6/1994 |
| EP | 0 607 435 | 7/1994 |
| EP | 0 682 266 | 11/1995 |
| EP | 0 875 922 | 11/1998 |
| EP | 0 964 259 | 12/1999 |
| EP | 0 999 600 | 5/2000 |
| EP | 1 001 468 | 5/2000 |
| EP | 1 109 212 | 6/2001 |
| GB | 1 319 311 | 6/1970 |
| GB | 2 335 792 | 9/1999 |
| JP | 52-88354 | 7/1977 |
| JP | 54-134554 | 10/1979 |
| JP | 55-87424 | 7/1980 |
| JP | 57-118683 | 7/1982 |
| JP | 58-213412 | 12/1983 |
| JP | 60-210018 | 10/1985 |
| JP | 60-212018 | 10/1985 |
| JP | 61-63015 | 4/1986 |
| JP | 61-108187 | 5/1986 |
| JP | 63-34994 | 2/1988 |
| JP | 63-131104 | 6/1988 |
| JP | 63-198365 | 8/1988 |
| JP | 1-102435 | 4/1989 |
| JP | 2-391 | 1/1990 |
| JP | 63-278629 | 1/1990 |
| JP | 5-48072 | 2/1993 |
| JP | 6-232126 | 8/1994 |
| JP | 6-291299 | 10/1994 |
| JP | 6-33 4168 | 12/1994 |
| JP | 0812494 | 1/1996 |
| JP | 10-321943 | 12/1998 |
| JP | 11-238683 | 8/1999 |
| JP | 11-260835 | 9/1999 |
| WO | WO 92/10875 | 6/1992 |
| WO | WO 97/45827 | 12/1997 |
| WO | WO 99/14797 | 3/1999 |
| WO | WO 99/14804 | 3/1999 |
| WO | WO 99/19546 | 4/1999 |
| WO | WO 99/63580 | 12/1999 |
| WO | WO 00/33363 | 6/2000 |
| WO | WO 00/48239 | 8/2000 |

OTHER PUBLICATIONS

W. F. Egelhoff et al., "Optimizing GMR Spin Valves: The Outlook for Improved Properties", *1998 Int'l Non Volatile Memory Technology Conference*, pp. 34–37.

Wang et al., "Processing and Performance of Piezoelectric Films," Univ. Of MD, Wilcoxon Research Col, and Motorola Labs, May 11, 2000.

M. Rotter et al., "Nonlinear Acoustoelectric Interactions in GaAs/LiNbO$_3$ Structures", *Applied Physics Letters*, vol. 75(7), Aug. 16, 1999, pp. 965–967.

K. Sreenivas et al., "Surface Acoustic Wave Propagation on Lead Zirconate Titanate Thin Films, " *Appl. Phys. Lett.* 52 (9), Feb. 29, 1998, pp. 709–711.

M. Rotter et al., "Single Chip Fused Hybrids for Acousto–Optic Applications," *1997 Applied Physics Letters*, vol. 70(16), Apr. 21, 1997, pp. 2097–2099.

A. Mansingh et al., "Surface Acoustic Wave Propagation in PZT/YBCO/SrTiO$_3$ and PbTiO$_3$/epitaxial Heterostructures," *Ferroelectric*, vol. 224, pp. 275–282, 1999.

S. Mathews et al., "Ferroelectric Field Effect Transistor Based on Epitaxial Perovskite Heterostructures ", *Science*, vol. 276, Apr. 11, 1997, pp. 238–240.

R. Houdre et al., "Properties of GaAs on Si Grown by Molecular Beam Epitaxy," *Solid State and Materials Sciences*, vol. 16, Iss. 2, 1990, pp. 91–114.

S. F. Fang et al., "Gallium Arsenide and Other Compound Semiconductors on Silicon," *J. Appl. Phys.*, 68(7), Oct. 1, 1990, pp. R31–R58.

Carlin et al., Impact of aAs Buffer Thickness on Electronic Quality of GaAs Grown on Graded Ge/GeSi/Si Substrates, *Appl. Phys. Letter*, vol. 76, No. 14, April 2000, pp. 1884–1886.

Ringel et al., "Epitaxial Integration of III–V Materials and Devices with Si Using Graded GeSi Buffers," 27th International Symposium on Compound Semiconductors, Oct. 2000.

Zogg et al., "Progress in Compound–Semiconductor–on–Silicon–Heteropitaxy with Fluoride Buffer Layers," *J. Electrochem Soc.*, vol. 136, No. 3, March 1998, pp. 775–779.

Xiong et al., "Oxide Defined GaAs Vertical–Cavity Surface–Emitting Lasers on Si Substrates," *IEEE Photonics Technology Letters*, vol. 12, No. 2, Feb. 2000, pp. 110–112.

Clem et al., "Investigation of PZT//LSCO//Pt//Aerogel Thin Film Composites for Uncooled Pyroelectric IR Detectors," *Mat. Res. Soc. Symp. Proc.*, vol. 541, pp. 661–666, 1999.

Gunapala et al., "Bound–To–Quasi–Bound Quantum–Well Infrared Photodetectors," NASA Tech Brief, vol. 22, No. 9, September 1998.

Brown et al., "Photodetectors: Materials and Devices II," *Intn. Society for Optical Engineering, vol. 2999*, pp. 211–224.

Bruley et al., "Nanostructure and Chemistry of a (100)MgO/(100) GaAs Interface," *Appl. Phys. Lett*, 65(5), Aug. 1994, pp. 564–566.

Fork et al., "Epitaxial MgO On Si(001) for Y–Ba–Cu–O Thin Film Growth by Pulsed Laser Deposition," *Appl. Phys. Lett.*, 58(20), May 20, 1991, pp. 2294–2296.

Himpsel et al., "Dialectrics on Semiconductors," *Materials Science and Engineering*, B1(1988), pp. 9–13.

Li et al., "Epitalial La$_{0.67}$Sr$_{0.33}$MnO$_3$Magnetic Tunnel Junctions," *J. Appl. Phys.*81(8), Apr. 15, 1997, pp. 5509–5511.

O'Donnell et al., "Colossal Magnetoresistance Magnetic Tunnel Junctions Grown by Molecular–Bearm Epitaxy," *Appl. Physic Letters*, vol. 76, No. 114, Apr. 3, 2000, pp. 1914–1916.

Mikami et al., "Formation of Si Epi/MgO–Al$_2$O$_3$Epi./SiO$_3$/Si and its Epitaxial Film Quality," *Fundamental Research Laboratories and Microelectronics Laboratories*, pp. 31–34, 1983.

T. Asano et al., "An Epitaxial Si/Insulator/Si Structure Prepared by Vacuum Deposition of CaF$_2$ and Silicon," *Thin Solid Films*, vol. 93 (1982), pp. 143–150.

T. Chikyow et al., "Reaction and Regrowth Control of CeO$_2$ on Si(111) Surface for the Silicon–On–Insulator Structure," *Appl. Phys. Lett.*, vol. 65, No. 8, Aug. 22, 1994, pp. 1030–1032.

J.F. Kang, et al., "Epitaxial Growth of CeO$_2$(100) Films on Si(100) Substrates by Dual Ion Beams Reactive Sputtering," *Solid State Communications*, vol. 108, No. 4, pp. 225–227, 1998.

R. A. Morgan et al., "Vertical–Cavity Surface–Emitting Lasers Come of Age," *SPIE*, vol. 2683, pp. 18–29.

"Technical Analysis of Qualcomm QCP–800 Portable Cellular Phone (Transmitter Circuitry)," Talus Corporation Qualcomm QCP–800 Technical Analysis Report, Dec. 10, 1996, pp. 5–8.

Jo–Ey Wong, et al.; "An Electrostatically–Actuated MEMS Switch For Power Applications," *IEEE*, 2000; pp. 633–638.

T. Mizuno, et al.; "Electron and Hole Mobility Enhancement in Strained–Si MOSFET's on SiGe–on–Insulator Substrates Fabricated by SIMOX Technology"; , *IEEE Electron Device Letters*, vol. 21, No. 5, May 2000; pp. 230–232.

F.M. Buffer, et al.; "Strain–dependence of electron transport in bulk Si and deep–submicron MOSFET's " Computatural Electronics, 2000, Book of Abstracts, IWCE Glasgow 2000, 7$^{th}$ Int'l Workshop on, 2000; pp. 64–65.

S.S. Lu, et al.; "Piezoelectric field effect transistor (PEFET) using In$_{0.2}$Ga$_{0.8}$As/Al$_{0.65}$As/In$_{0.2}$Ga$_{0.8}$As/GaAs Strained layer structure on (111)B GaAs substrate"; *Electroics Letters*, 12$^{th}$Ma 1994, vol. 30, No. 10, pp. 823–825.

Kihong Kim, et al. On–Chip Wireless Interconnection with Integrated Antennas; 2000 IEEE; pp. 20.2.1–20.3.4.

G. Passiopoulos, et al.; "V–Band Single Chip, Direct Carrier BPSK Modulation Transmitter with Integrated Patch Antenna"; 1998 IEEE MTT–S Digest; pp. 305–308.

Mau–Chung Frank Chang, et al., "RF/Wireless Interconnect for Inter–and Intra–Chip Communications"; Proceedings of the IEEE, vol. 89, No. Apr. 2001, pp. 456–466.

The Electronics Industry Report; Prismark; 2001; pp. 111–120.

J. K. Abrokwah, et al.; "A Manufacturable Complementary GaAs Process"; GaAs IC Symposium IEEE, 1993; pp. 127–130.

H. Nagata, "A Preliminary Consideration of the Growth Behaviour of CeO$_2$, SrTiO$_3$ and SrVO$_3$Films on Si Substrate," *Thin Solid Films*, 224, 1993, pp. 1–3.

Nagata et al., "Heteroepitaxial Growth of CeO$_2$(001) Films on Si(001) Substrates by Pulsed Laser Deposition in Ultrahigh Vacuum," *Jpn. Jour. Appl. Phys., vol. 30*, No. 6B, June 1991, pp. L1136–L1138.

Kado et al., "Heteroepitaxial Growthof SrO Films on Si Substrates," *J. Appl. Phys.*, 61(6), Mar. 15, 1987, pp. 2398–2400.

Bean et al., "Silicon Molecular Beam Eptaxy," *Materials Research Symposium Proceedings*, vol. 220, pp. 595–600, Apr. 29 –May 3, 1991.

J. K. Abrokwah, et al.; "A Manufacturable H9gh–Speed Low–Power Complementary GaAs Process"; Extended Abstracts of the 1994 International Conference on Solid State Devices and Materials, Yokohama, 1994, pp. 592–594.

Leonard J. Brillson; "Stable and Epitaxial Contacts to III–V Compound Semiconductors"; Semiconductors Fundamentals and Technology; Noyles Publications, 1993; pp. 67–150.

Jayshri Sabarinathat, et al.; "Submicron three–dimensional infrared GaAs/Al$_x$O$_y$–based photonic crystal using single–step epithaxial growth"; *Applied Physics Letters*, vol. 78, No. 20, May 14, 2001; pp. 3024–3026.

Philip Ball; "The Next Generation of Optical Fibert", Technology Review, May 2001; pp. 55–61.

John D. Joannopoulos, et al.; "Molding the Flow of Light"; Photonic Crystals; Princeton University Press, 1995.

Thomas F. Krauss, et al.; "Photonic crystals in the optical regime –past, present and future"; Progress in Quantum Electronics 23 (1999) 51–96.

G. H. Jin, et al.; "PLZT Film Waveguide Mach–Zehnder Electrooptic Modulator"; *Journal of Lightwave Technology*, vol. 18, No. 6, June 2000; pp. 807–812.

D.E. Aspnes, et al.; "Steps on (001) silicon surfaces"; *J. Vac. Sci. Technol. B*, vol. 5, No. 4, Jul./Aug. 1987; pp. 939–944.

D.M. Newns, et al.; "Mott transition field effect transistor"; *Applied Physics Letters*, vol. 73, No. 6, Aug. 10, 1998; pp. 780–782.

Lucent Technologies, Inc. Arrayed Waveguide Grating Multiplexer/Demultiplexer, ; January 2000; 4 pages.

Hisashi Shichijo, et al.; "Co–Integration of GaAs MESFET and Si CMOS Circuits"; *IEEE Electron Device Letters*, vol. 9, No. 9, September 1988; pp. 444–446.

H. Shichijo, et al.; "GaAs MESFET and Si CMOS Cointegration and Circuit Techniques," 1988 *IEEE Electron Device Letters*, vol. 9, No. 9, September 1988; pp. 444–446.

H. Shichijo, et al.; "Monolithic Process for Co–Integration of GaAs and Silicon Circuits"; IEEE; pp. 778–781.

Z.H. Zhu, et al. "Growth of InGaAs multi–quantum wells at 1.3 µm wavelength on GaAs compliant substrates", *Applied Physics Letters*, vol. 72, No. 20, May 18, 1998; pp. 2598–2600.

Kurt Eisenbeiser, et al.; "Metamorphic InAlAs/InGaAs Enhancement Mode HEMT's on GaAs Substrates", *IEEE Electron Device Letters*, vol. 20, No. 10, October 1999; pp. 507–509.

Tomonori Nagashma, et al.; "Three–Terminal Tandem Solar Cells with a Back–Contact Type Bottom Cell" Higashifuji Technical Center, Toyota Motor Corporation; 4 pages.

James Schellenberg, et al.; "Low–Loss, Planar Monolithic Baluns for K/Ka–Band Applications"; 1999 IEEE MTT-S Digest; pp. 1733–1736.

Patent Abstracts of Japan, vol. 010, No. 289, Oct. 2, 1986 & JP 61 108187, May 26, 1986.

Patent Abstracts of Japan, vol. 017, No. 344 & JP 05 048072, Feb. 26, 1993.

Patent Abstracts of Japan, vol. 1999, No. 14, Dec. 22, 1999 & JP 11 260835, sep. 24, 1999.

Patent Abstracts of Japan, vol. 012, No. 388, Oct. 17, 1988 & JP 63 131104, Jun. 3, 1988.

Patent Abstracts of Japan, vol. 012, No. 246, Jul. 12, 1988 & JP 63 034994, Feb. 15, 1988.

Patent Abstracts of Japan, vol. 012, No. 077, Mar. 10, 1988 & JP 62 216600, Sep. 24, 1987.

R.D. Vispute; "High quality optoelectronic grade epitaxial AIN Films on $\alpha-Al_2O_3$, Si and 6H–SiC by pulsed laser deposition"; Thin Solid Films 299 (1997), pp. 94–103.

T. Warren Weeks, et al.; "GaN thin films deposited via organometallic vapor phase epitaxy on $\alpha(6H)$–SiC(0001) using high–temperature monocrystalline AIN Buffer layers", *320 Applied Physics Letters*, vol. 67, No. 3, Jul. 17, 1995, pp. 1401–1403.

Z. Yu, et al.; "Epitaxial oxide thin films on SI(001)"; *J. Vac. Sci. Technol.*, B. Vol. 18, No. 4, Jul./Aug. 2000; pp. 2139–2145.

Patent Abstracts of Japan, vol. 015, No. 098, Mar. 8, 1991 & JP 02 306680. Dec. 20, 1990.

Peter S. Guilfoyle, et al.; "Optoelectronic Architecture for High–Speed Switching and Processing Applications"; 1998 The Photonics Design and Applications Handbook; pp. H–399–H–406.

McKee et al., "$BaSi_2$ and Thin Film Alkaline Earth Silicides on Silicon," *Appl. Phys. Lett.*, 63 (20), Nov. 1993, pp. 2818–2820.

McKee et al., "Surface Structures and the Orthorhombic Transformation of Thin Film $BaSi_2$ on Silicon," *Mat. Res. Soc. Symp. Proc.*, vol. 221, pp. 131–136.

"Integration of GaAs on Si Using a Spinel Buffer Layer", IBM Technical Bulletin, vol. 30, No. 6, No. 1987, p. 365.

"GaInAs Superconducting FET," IBM Technical Bulletin, vol. 36, No. 8, Aug. 1993, pp. 655–656.

"Epitaxial 3d Structure Using Mixed Spinels," IBM Technical Bulletin, vol. 30, No. 3, Aug. 1987, p. 1271.

Moon et al., "Roles of Buffer Layers in Epitaxial Growth of $SrTiO_3$ Films on Silicon Substrates," *Japan J of Appl. Phys.*, vol. 33, Mar. 1994, pp. 1472–1477.

Yodo et al., GaAs Heteroepitaxial Growth on Si Substrates with Thin Si Interlayers in situ Annealed at High Temperatures, 8257b *J. of Vacuum Science & Technology*, 1995 May/Jun., vol. 13, No. 3, pp. 1000–1005.

Cuomo et al., "Substrate Effect on the Superconductivity of $YBa_2Cu_3O_7$ Thin Films," AIP Conference 1988, pp. 141–148.

McKee et al., "Crystalline Oxides on Silicon: The First Five Monolayers," *Physical Review Letters*, vol. 81, No. 14, Oct. 1998, pp. 3014–3017.

McKee et al., "Molecular Beam Epitaxy Growth of Epitaxial Barium Silicide, Barium Oxide, and Barium Titanate and Silicon," *1991 American Institute of Physics*, pp. 782–784, Aug. 13, 1991.

Tambo et al., Molecular Beam Epitaxy Growth of $SrTiO_3$Films on Si(100)–2x1 with SrO Buffer Layer, *Jpn. J. Appl. Phys.*, vol. 37, 1998, pp. 4454–4459.

McKee et al., "The MBE Growth and Optical Qualtiy of $BaTiO_3$ and $SrTiO_3$ Thin Films on MgO," *Mat. Res. Soc. Symp. Proc.*, vol. 341, Apr. 1994, pp. 309–314.

Brian A. Floyd, et al., "The projected Power Consumption of a Wireless Clock Distribution System and Comparison to Conventional Distribution Systems", IEEE, 1999; pp. IITC99—250.

Mori et al., "Epitaxial Growth of $SrTiO_3$Films on Si(100) Substrates Using a Focused Electron Beam Evaporation Method," *Jpn. J. of Apl. Phys.*, vol. 30, No. 8A, Aug. 1991, pp. L1415–L1417.

Moon et al., "Growth of Crystalline $SrTiO_3$ Films on Si Substrates Using Thin Fluoride Buffer Layers and Their Electrical Properties," *Jpn. J. of Appl. Phys.*, vol. 33, (1994), pp. 5911–5916.

Farrow et al., "Heteroepitaxy of Dissimilar Materials," *Mat. Res. Soc. Symposium Proceedings*, vol. 221, pp. 29–34, Apr. 29 –May 2, 1991.

Choi et al., "Heteroepitaxy on Silicon: Fundamentals, Structure, and Devices,", *Mat. Res. Soc.*, Symposium Proceedings, vol. 116, pp. 369–374, Apr. 5–8, 1988.

Douglas B. Chrisey, et al; Pulsed Laser Deposition of Thin Films; pp. 273–285.

B.A. Block, et al; "Photoluminescence properties of $Er^3$–doped $BATiO_3$thin films", Appl. Phys. Lett. 65(1), Jul. 4, 1994, pp. 25–27.

Gentex Corporate Website; Photoelectric Smoke Detectors –How They Work; 2001.

Jeffrey B. Casady, et al.; "A Hybrid 6H–SiC Temperature Sensor Operational from 25°to 500°": IEEE Transactions on Components, Packaging, and Manufacturing Technology –Part A, vol. 19, No. 3, Sep. 1996; pp. 416–422.

Ronald W. Waynant, et al.; "Optoelectronic Integrated Circuits", Electro–Optics Handbook, McGraw–Hill, Inc., 1994; Chapter Twenty Seven.

Antonio Mecozzi, et al.; "The Roles of Semiconductor Optical Amplifiers in Optical Networks "; Optics & Photonics News; March 2001; pp. 37–42.

D.A. Francis, et al.; "A single–chip linear optical amplifier"; OFC, 2001; Mar. 17–22, 2001.

Kevin J. Chen et al; "A Novel Ultrafast Functional Device: Resonant Tunneling High Electron Mobility Transistor"; Electron Devices Meetingk 1996; IEEE Hong Kong; Jun. 29, 1996; pp. 60–63, XP010210167.

Stephen A. Mass; "Microwave Mixers"; Second Edition; 2pp.

Wen–Ching Shih et al.; "Theoretical Investigation of the SAW Properties of Ferroelectric Film Composite Structures"; IEEE Transactions of Ultrasonics, Ferroelectrics, and Frequency Control; vol. 45, No. 2, Mar. 1998; pp. 305–316.

Zhu Dazhong et al.; "Design of $ZnO/SiO_2/Si$ Monolithic Integrated Programmable SAW Filter"; Proceedings of Fifth International Conference on Solid–State and Integrated Circuit Technology; Oct. 21–23; 1998; pp. 826–829.

Kirk–Othmer Encyclopedia of Chemical Technology; Fourth Edition, vol. 12; Fuel Resources to Heat Staibilizers; A Wiley–Interscience Publication; John Wiley & Sons.

John W. Goodman et al; "Optical Interconnections For VLSI Systems"; Proceedings of the IEEE, vol. 72, No. 7 Jul. 1984.

Fathimulla et al.; "Monolithic Integration of InGaAs/InAIAs MODFETs and RTDs on InP–bonded–to Si Substrate"; Fourth International Conference on Indium Phosphide and Related Materials, Newport, RI, USA; Apr. 21–24, 1992; pp. 167–170; XP000341253; IEEE, New York, NY, USA; ISBN: 0–7803–0522–1.

Pierret, R.F.; "1/J–FET and MESFET"; Field Effect Devices; MA, Addison–Wesley; 1990; pp. 9–22.

S.N. Subbarao et al.; "Monolithic Pin Photodetector and FET Amplifier on GaAs–on–Si"; GaAs IC Symposium; 1989 IEEE; pp. 163–166.

Don W. Shaw; "Epitaxial GaAs on Si: Progress and Potential Applications"; Materials Research Society Symposia Proceedings; vol. 91; pp. 15–30; 1987.

Umesh K. Mishra et al.; "Oxide Based Compound Semiconductor Electronics"; Department of Electrical & Computer Engineering and Materials Department; IEEE; 1997; pp. 21.1.1–21.1.4.

* cited by examiner

APPARATUS AND METHOD FOR MEASURING SELECTED PHYSICAL CONDITION OF AN ANIMATE SUBJECT

FIELD OF THE INVENTION

Apparatuses for medical diagnostic measurement of physical conditions of animate subjects, such as human subjects or veterinary subjects, are often too bulky and too inefficient in their power consumption to be convenient for use. These limitations are especially disadvantageous when the desired use for such a diagnostic device is as a monitor for a condition associated with the subject. Such diagnostic devices would benefit from improved high speed communications among individual components within products or among products.

It is known, for example, that light absorption in tissue can be used to monitor changes in blood oxygenation and hematocrit (concentration of red blood cells). Generally, a light source, such as a laser, is used to illuminate the tissue being tested and resultant light is measured to identify a particular physical condition. Resultant light may be, for example, refracted light transmitted from one side of tissue through the tissue and received at an opposing side of the tissue. Resultant light may also include scattered reflected light that is detected on the same side of the tissue at which illumination is being effected.

Prior art apparatuses that employ such technology for medical or veterinary diagnostics, or other measurement of physical conditions of animate subjects, include several discrete devices, such as a laser, a light detector communications devices, data processing devices, and other devices. The cumbersome packaging that is necessitated by the employment of such discrete devices, and the necessary interconnecting wires, optic fibers, I/O (input/output) devices and other sundry components have been a barrier to widespread use of such devices, a barrier founded in high cost and inconvenience. The resultant bulky packaging for such discrete component products has particularly been a barrier to products that are easy enough to use and unobtrusive enough to employ to encourage use of the products as a "wearable" item for convenient continuous monitoring of an animate subject. Such wearable objects could include, for example, jewelry or articles of clothing.

Such prior art devices implemented in discrete components require interfaces such as high speed buses, I/O (input/output) interfaces for optical links or high speed RF (radio frequency) links, or other interface structures. Integration of the several devices that comprise a product into a unitary structure eliminates the need for some of the interfaces required for signal hand off, buffering and other functions that must be accomplished in a multi-element product. Prior art fabrication techniques available for producing unitary structures involving various semiconductor materials have proven prohibitively costly and space-inefficient to yield significant improvements by unifying structures.

A monolithic structure that achieves device unitary structure at the fabrication level reduces the need for individual I/O interfaces for each module transition, and thereby eliminates the need for on-chip "real estate" to accommodate such I/O interfaces. Other advantages realized by such a cost-efficient unitary fabrication ability include a significant reduction in size, an increase in operating speed, a reduction of electromagnetic noise and radiation emanations, an increase in performance reliability, a reduction in cost of manufacture and lower operating power requirements with an attendant lower cost of operation.

A capability for truly unitary fabrication employing a variety of semiconductor manufacturing technologies provides opportunities to produce multi-technology unitary structures that meet a wide variety of needs. For example, unitary structures may be fabricated to satisfy a wide variety of communication standards, such as cellular telephone standards, personal communication system (PCS) standards, "Bluetooth" communication standards, and other industry-wide standards. Such compact construction capabilities permit manufacture of medical diagnostic products that are convenient to use, have long battery life, generate less radiation and electromagnetic noise, perform continuously, are lower in cost, and communicate test results reliably and cheaply, among other benefits.

Such advantages are particularly valuable in the manufacture of medical diagnostic and monitoring devices. Physical conditions such as heart rate, temperature, blood pressure, hematocrit (concentration of red blood cells), and other conditions may be continuously monitored or checked on command with convenient compact nonintrusive devices. Such devices may be fashioned to periodically sample, or check, a particular physical condition, compare a test result with a predetermined threshold or other criterion, and notify a remote user when the threshold or other criterion is met or exceeded. Such monitor equipment may be made compact enough to be integrally included into watches, jewelry, or other wearable items, including articles of clothing.

There is a need for a compact diagnostic monitoring device manifested in a cost-effective power-efficient integrated unitary structure, especially including a communication capability. Communications may be effected by any of various media: optic coupling, radio frequency coupling, sonic coupling, inductive coupling, capacitive coupling, magnetic coupling, or other communication media.

This invention relates generally to semiconductor structures and devices for medical diagnostic devices, including monitoring devices. This invention more specifically relates to compound semiconductor structures and devices and to the fabrication and use of semiconductor structures, devices, and integrated circuits that include a monocrystalline compound semiconductor material.

BACKGROUND OF THE INVENTION

The preferred embodiment of the present invention is an apparatus for measuring at least one selected physical condition of an animate subject. The apparatus comprises: (a) a light source; (b) a light receiver; the light receiver receives resultant light from the light source via the subject; and (c) an information processor connected with at least the light receiver. The processor receives indication of the resultant light from the light receiver and evaluates the indication to effect the measuring. The processor is implemented in a unitary structure with at least one of the light source and the light detector. The unitary structure is borne upon a single silicon substrate. The apparatus may further comprise at least one first interface element coupled with the processor and with at least the light receiver. The first interface element facilitates communication with the processor. The first interface element is implemented in the unitary structure. The apparatus may even further comprise at least one second interface element coupled with the processor. The second interface element includes communication means for conveying messages to loci remote from the apparatus. The second interface element is implemented in the unitary structure.

The method of the present invention comprises the steps of: (a) providing a light source for illuminating the subject; (b) providing a light receiver for receiving resultant light from the subject; (c) providing an information processor connected with at least the light receiver for receiving indication of the resultant light from the light receiver; and (d) evaluating the indication to effect the measuring. The processor is implemented in a unitary structure with at least one of the light source and the light detector. The unitary structure is borne upon a single silicon substrate.

The unitary structure is comprised of a monolithic structure. At least a first portion of the monolithic structure is implemented in silicon, and at least a second portion of the monolithic structure is implemented in at least one compound semiconductor material.

The vast majority of semiconductor discrete devices and integrated circuits employed for medical diagnostic applications, including hematological and other measurements of physical conditions of animate subjects, such as humans, are fabricated from silicon, at least in part because of the availability of inexpensive, high quality monocrystalline silicon substrates. Other semiconductor materials, such as the so called compound semiconductor materials, have physical attributes, including wider bandgap and/or higher mobility than silicon, or direct band gaps that makes these materials advantageous for certain types of semiconductor devices. Unfortunately, compound semiconductor materials are generally much more expensive than silicon and are not available in large wafers as is silicon. Gallium arsenide (GaAs), the most readily available compound semiconductor material, is available in wafers only up to about 150 millimeters (mm) in diameter. In contrast, silicon wafers are available up to about 300 mm and are widely available at 200 mm. The 150 mm GaAs wafers are many times more expensive than are their silicon counterparts. Wafers of other compound semiconductor materials are even less available and are more expensive than GaAs.

Because of the desirable characteristics of compound semiconductor materials, and because of their present generally high cost and low availability in bulk form, for many years attempts have been made to grow thin films of the compound semiconductor materials on a foreign substrate. To achieve optimal characteristics of the compound semiconductor material, however, a monocrystalline film of high crystalline quality is desired. Attempts have been made, for example, to grow layers of a monocrystalline compound semiconductor material on germanium, silicon, and various insulators. These attempts have generally been unsuccessful because lattice mismatches between the host crystal and the grown crystal have caused the resulting thin film of compound semiconductor material to be of low crystalline quality.

If a large area thin film of high quality monocrystalline compound semiconductor material was available at low cost, a variety of semiconductor devices could advantageously be fabricated in that film at a low cost compared to the cost of fabricating such devices on a bulk wafer of compound semiconductor material or in an epitaxial film of such material on a bulk wafer of compound semiconductor material.

In addition, if a thin film of high quality monocrystalline compound semiconductor material could be realized on a bulk wafer such as a silicon wafer, an integrated device structure could be achieved that took advantage of the best properties of both the silicon and the compound semiconductor material.

Accordingly, a need exists for a semiconductor structure that provides a high quality monocrystalline compound semiconductor film over another monocrystalline material and for a process for making such a structure.

BRIEF DESCRIPTION OF THE DRAWINGS

The present invention is illustrated by way of example and not limitation in the accompanying figures, in which like references indicate similar elements, and in which.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE DRAWINGS

Figure 1:
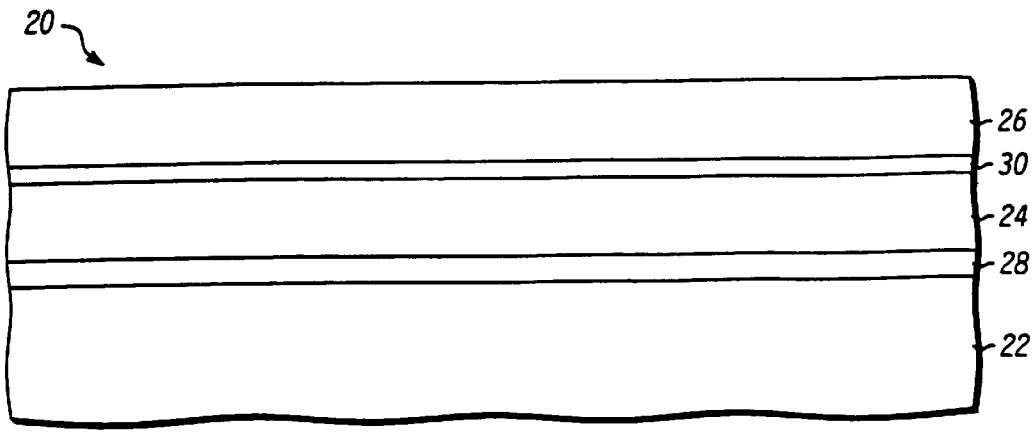
FIGS. 1–3 illustrate schematically, in cross section, device structures in accordance with various embodiments of the invention.

FIG. 1 illustrates schematically, in cross section, a portion of a semiconductor structure 20 in accordance with an embodiment of the invention. Semiconductor structure 20 includes a monocrystalline substrate 22, accommodating buffer layer 24 comprising a monocrystalline material, and a layer 26 of a monocrystalline compound semiconductor material. In this context, the term "monocrystalline" shall have the meaning commonly used within the semiconductor industry. The term shall refer to materials that are a single crystal or that are substantially a single crystal and shall include those materials having a relatively small number of defects such as dislocations and the like as are commonly found in substrates of silicon or germanium or mixtures of silicon and germanium and epitaxial layers of such materials commonly found in the semiconductor industry.

In accordance with one embodiment of the invention, structure 20 also includes an amorphous intermediate layer 28 positioned between substrate 22 and accommodating buffer layer 24. Structure 20 may also include a template layer 30 between the accommodating buffer layer and compound semiconductor layer 26. As will be explained more fully below, the template layer helps to initiate the growth of the compound semiconductor layer on the accommodating buffer layer. The amorphous intermediate layer helps to relieve the strain in the accommodating buffer layer and by doing so, aids in the growth of a high crystalline quality accommodating buffer layer.

Substrate 22, in accordance with an embodiment of the invention, is a monocrystalline semiconductor wafer, preferably of large diameter. The wafer can be of a material from Group IV of the periodic table, and preferably a material from Group IVA. Examples of Group IV semiconductor materials include silicon, germanium, mixed silicon and germanium, mixed silicon and carbon, mixed silicon, germanium and carbon, and the like. Preferably substrate 22 is a wafer containing silicon or germanium, and most preferably is a high quality monocrystalline silicon wafer as used in the semiconductor industry. Accommodating buffer layer 24 is preferably a monocrystalline oxide or nitride material epitaxially grown on the underlying substrate. In accordance with one embodiment of the invention, amorphous intermediate layer 28 is grown on substrate 22 at the interface between substrate 22 and the growing accommodating buffer layer by the oxidation of substrate 22 during the growth of layer 24. The amorphous intermediate layer serves to relieve strain that might otherwise occur in the monocrystalline accommodating buffer layer as a result of differences in the lattice constants of the substrate and the buffer layer. As used herein, lattice constant refers to the distance between atoms of a cell measured in the plane of the surface. If such strain is not relieved by the amorphous intermediate layer, the strain may cause defects in the crystalline structure of the accommodating buffer layer. Defects in the crystalline structure of the accommodating buffer layer, in turn, would make it difficult to achieve a high quality crystalline structure in monocrystalline compound semiconductor layer 26.

Accommodating buffer layer 24 is preferably a monocrystalline oxide or nitride material selected for its crystalline compatibility with the underlying substrate and with the overlying compound semiconductor material. For example, the material could be an oxide or nitride having a lattice structure matched to the substrate and to the subsequently applied semiconductor material. Materials that are suitable for the accommodating buffer layer include metal oxides such as the alkaline earth metal titanates, alkaline earth metal zirconates, alkaline earth metal hafnates, alkaline earth metal tantalates, alkaline earth metal ruthenates, alkaline earth metal niobates, alkaline earth metal vanadates, perovskite oxides such as alkaline earth metal tin-based perovskites, lanthanum aluminate, lanthanum scandium oxide, and gadolinium oxide. Additionally, various nitrides such as gallium nitride, aluminum nitride, and boron nitride may also be used for the accommodating buffer layer. Most of these materials are insulators, although strontium ruthenate, for example, is a conductor. Generally, these materials are metal oxides or metal nitrides, and more particularly, these metal oxide or nitrides typically include at least two different metallic elements. In some specific applications, the metal oxides or nitride may include three or more different metallic elements.

Amorphous interface layer 28 is preferably an oxide formed by the oxidation of the surface of substrate 22, and more preferably is composed of a silicon oxide. The thickness of layer 28 is sufficient to relieve strain attributed to mismatches between the lattice constants of substrate 22 and accommodating buffer layer 24. Typically, layer 28 has a thickness in the range of approximately 0.5–5 nm.

The compound semiconductor material of layer 26 can be selected, as needed for a particular semiconductor structure, from any of the Group IIIA and VA elements (III-V semiconductor compounds), mixed III–V compounds, Group II (A or B) and VIA elements (II–VI semiconductor compounds), and mixed II–VI compounds. Examples include gallium arsenide (GaAs), gallium indium arsenide (GaInAs), gallium aluminum arsenide (GaAlAs), indium phosphide (InP), cadmium sulfide (CdS), cadmium mercury telluride (CdHgTe), zinc selenide (ZnSe), zinc sulfur selenide (ZnSSe), and the like. Suitable template materials chemically bond to the surface of the accommodating buffer layer 24 at selected sites and provide sites for the nucleation of the epitaxial growth of the subsequent compound semiconductor layer 26. Appropriate materials for template 30 are discussed below.

Figure 2:
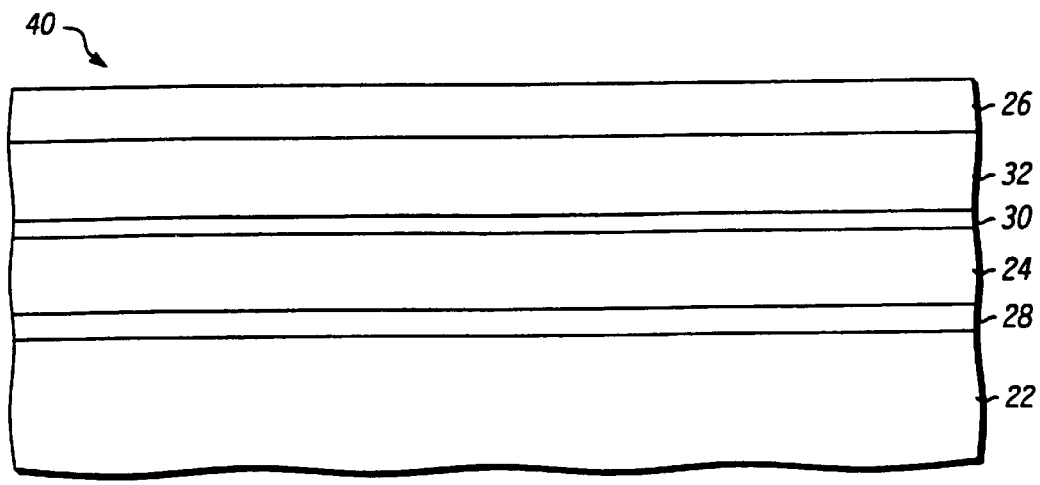

FIG. 2 illustrates, in cross section, a portion of a semiconductor structure 40 in accordance with a further embodiment of the invention. Structure 40 is similar to the previously described semiconductor structure 20, except that an additional buffer layer 32 is positioned between accommodating buffer layer 24 and layer of monocrystalline compound semiconductor material 26. Specifically, the additional buffer layer is positioned between template layer 30 and the overlying layer of compound semiconductor material. The additional buffer layer, formed of a semiconductor or compound semiconductor material, serves to provide a lattice compensation when the lattice constant of the accommodating buffer layer cannot be adequately matched to the overlying monocrystalline compound semiconductor material layer.

Figure 3:
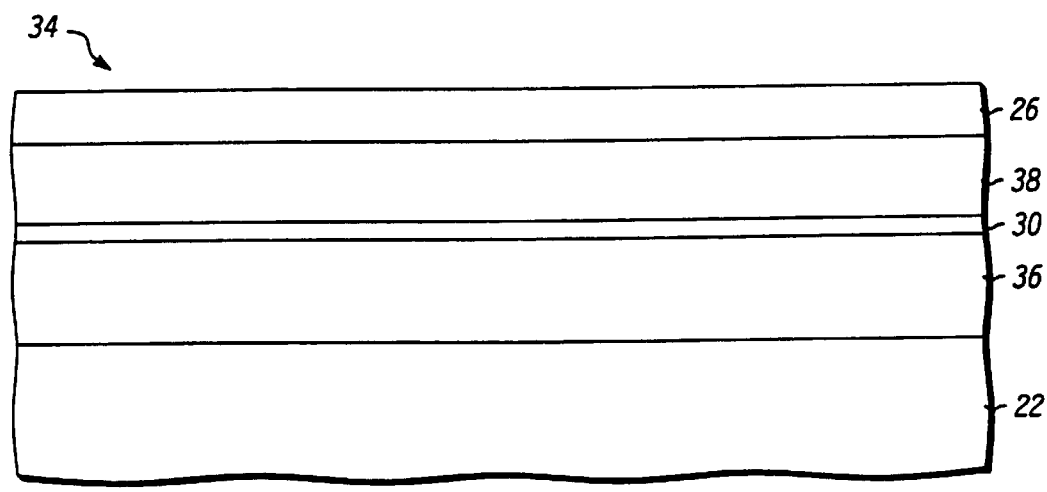

FIG. 3 schematically illustrates, in cross section, a portion of a semiconductor structure 34 in accordance with another exemplary embodiment of the invention. Structure 34 is similar to structure 20, except that structure 34 includes an amorphous layer 36, rather than accommodating buffer layer 24 and amorphous interface layer 28, and an additional semiconductor layer 38.

As explained in greater detail below, amorphous layer 36 may be formed by first forming an accommodating buffer layer and an amorphous interface layer in a similar manner to that described above. Monocrystalline semiconductor layer 26 is then formed (by epitaxial growth) overlying the monocrystalline accommodating buffer layer. The accommodating buffer layer is then exposed to an anneal process to convert the monocrystalline accommodating buffer layer to an amorphous layer. Amorphous layer 36 formed in this manner comprises materials from both the accommodating buffer and interface layers, which amorphous layers may or may not amalgamate. Thus, layer 36 may comprise one or two amorphous layers. Formation of amorphous layer 36 between substrate 22 and semiconductor layer 38 (subsequent to layer 38 formation) relieves stresses between layers 22 and 38 and provides a true compliant substrate for subsequent processing—e.g., compound semiconductor layer 26 formation.

The processes previously described above in connection with FIGS. 1 and 2 are adequate for growing monocrystalline compound semiconductor layers over a monocrystalline substrate. However, the process described in connection with FIG. 3, which includes transforming a monocrystalline accommodating buffer layer to an amorphous oxide layer, may be better for growing monocrystalline compound semiconductor layers because it allows any strain in layer 26 to relax.

Semiconductor layer 38 may include any of the materials described throughout this application in connection with either of compound semiconductor material layer 26 or additional buffer layer 32. For example, layer 38 may include monocrystalline Group IV or monocrystalline compound semiconductor materials.

In accordance with one embodiment of the present invention, semiconductor layer 38 serves as an anneal cap during layer 36 formation and as a template for subsequent semiconductor layer 26 formation. Accordingly, layer 38 is preferably thick enough to provide a suitable template for layer 26 growth (at least one monolayer) and thin enough to allow layer 38 to form as a substantially defect free monocrystalline semiconductor compound.

In accordance with another embodiment of the invention, semiconductor layer 38 comprises compound semiconductor material (e.g., a material discussed above in connection with compound semiconductor layer 26) that is thick enough to form devices within layer 38. In this case, a semiconductor structure in accordance with the present invention does not include compound semiconductor layer 26. In other words, the semiconductor structure in accordance with this embodiment only includes one compound semiconductor layer disposed above amorphous oxide layer 36.

The following non-limiting, illustrative examples illustrate various combinations of materials useful in structures 20, 40, and 34 in accordance with various alternative embodiments of the invention. These examples are merely illustrative, and it is not intended that the invention be limited to these illustrative examples.

EXAMPLE 1

In accordance with one embodiment of the invention, monocrystalline substrate 22 is a silicon substrate oriented in the (100) direction. The silicon substrate can be, for example, a silicon substrate as is commonly used in making complementary metal oxide semiconductor (CMOS) integrated circuits having a diameter of about 200–300 mm. In accordance with this embodiment of the invention, accommodating buffer layer 24 is a monocrystalline layer of $Sr_zBa_{1-z}TiO_3$ where z ranges from 0 to 1 and the amorphous intermediate layer is a layer of silicon oxide ($SiO_x$) formed at the interface between the silicon substrate and the accommodating buffer layer. The value of z is selected to obtain one or more lattice constants closely matched to corresponding lattice constants of the subsequently formed layer 26. The accommodating buffer layer can have a thickness of about 2 to about 100 nanometers (nm) and preferably has a thickness of about 10 nm. In general, it is desired to have an accommodating buffer layer thick enough to isolate the compound semiconductor layer from the substrate to obtain the desired electrical and optical properties. Layers thicker than 100 nm usually provide little additional benefit while increasing cost unnecessarily; however, thicker layers may be fabricated if needed. The amorphous intermediate layer of silicon oxide can have a thickness of about 0.5–5 nm, and preferably a thickness of about 1.5–2.5 nm.

In accordance with this embodiment of the invention, compound semiconductor material layer 26 is a layer of gallium arsenide (GaAs) or aluminum gallium arsenide (AlGaAs) having a thickness of about 1 nm to about 100 micrometers ($\mu m$) and preferably a thickness of about 0.5 $\mu m$ to 10 $\mu m$. The thickness generally depends on the application for which the layer is being prepared. To facilitate the epitaxial growth of the gallium arsenide or aluminum gallium arsenide on the monocrystalline oxide, a template layer is formed by capping the oxide layer. The template layer is preferably 1–10 monolayers of Ti—As, Sr—O—As, Sr—Ga—O, or Sr—Al—O. By way of a preferred example, 1–2 monolayers of Ti—As or Sr—Ga—O have been shown to successfully grow GaAs layers.

EXAMPLE 2

In accordance with a further embodiment of the invention, monocrystalline substrate 22 is a silicon substrate as described above. The accommodating buffer layer is a monocrystalline oxide of strontium or barium zirconate or hafnate in a cubic or orthorhombic phase with an amorphous intermediate layer of silicon oxide formed at the interface between the silicon substrate and the accommodating buffer layer. The accommodating buffer layer can have a thickness of about 2–100 nm and preferably has a thickness of at least 5 nm to ensure adequate crystalline and surface quality and is formed of a monocrystalline $SrZrO_3$, $BaZrO_3$, $SrHfO_3$, $BaSnO_3$ or $BaHfO_3$. For example, a monocrystalline oxide layer of $BaZrO_3$ can grow at a temperature of about 700 degrees C. The lattice structure of the resulting crystalline oxide exhibits a 45 degree rotation with respect to the substrate silicon lattice structure.

An accommodating buffer layer formed of these zirconate or hafnate materials is suitable for the growth of compound semiconductor materials in the indium phosphide (InP) system. The compound semiconductor material can be, for example, indium phosphide (InP), indium gallium arsenide (InGaAs), aluminum indium arsenide, (AlInAs), or aluminum gallium indium arsenic phosphide (AlGaInAsP), having a thickness of about 1.0 nm to 10 $\mu m$. A suitable template for this structure is 1–10 monolayers of zirconium-arsenic (Zr—As), zirconium-phosphorus (Zr—P), hafnium-arsenic (Hf—As), hafnium-phosphorus (Hf—P), strontium-oxygen-arsenic (Sr—O—As), strontium-oxygen-phosphorus (Sr—O—P), barium-oxygen-arsenic (Ba—O—As), indium-strontium-oxygen (In—Sr—O), or barium-oxygen-phosphorus (Ba—O—P), and preferably 1–2 monolayers of one of these materials. By way of an example, for a barium zirconate accommodating buffer layer, the surface is terminated with 1–2 monolayers of zirconium followed by deposition of 1–2 monolayers of arsenic to form a Zr—As template. A monocrystalline layer of the compound semiconductor material from the indium phosphide system is then grown on the template layer. The resulting lattice structure of the compound semiconductor material exhibits a 45 degree rotation with respect to the accommodating buffer layer lattice structure and a lattice mismatch to (100) InP of less than 2.5%, and preferably less than about 1.0%.

EXAMPLE 3

In accordance with a further embodiment of the invention, a structure is provided that is suitable for the growth of an epitaxial film of a II–VI material overlying a silicon substrate. The substrate is preferably a silicon wafer as described above. A suitable accommodating buffer layer material is $Sr_xBa_{1-1}TiO_3$, where x ranges from 0 to 1, having a thickness of about 2–100 nm and preferably a thickness of about 5–15 nm. The II–VI compound semiconductor material can be, for example, zinc selenide (ZnSe) or zinc sulfur selenide (ZnSSe). A suitable template for this material system includes 1–10 monolayers of zinc-oxygen (Zn—O) followed by 1–2 monolayers of an excess of zinc followed by the selenidation of zinc on the surface. Alternatively, a template can be, for example, 1–10 monolayers of strontium-sulfur (Sr—S) followed by the ZnSSe.

EXAMPLE 4

This embodiment of the invention is an example of structure 40 illustrated in FIG. 2. Substrate 22, monocrystalline oxide layer 24, and monocrystalline compound semiconductor material layer 26 can be similar to those described in example 1. In addition, an additional buffer layer 32 serves to alleviate any strains that might result from a mismatch of the crystal lattice of the accommodating buffer layer and the lattice of the monocrystalline semiconductor material. Buffer layer 32 can be a layer of germanium or a GaAs, an aluminum gallium arsenide (AlGaAs), an indium gallium phosphide (InGaP), an aluminum gallium phosphide (AlGaP), an indium gallium arsenide (InGaAs), an aluminum indium phosphide (AlInP), a gallium arsenide phosphide (GaAsP), or an indium gallium phosphide (InGaP) strain compensated superlattice. In accordance with one aspect of this embodiment, buffer layer 32 includes a $GaAs_xP_{1-x}$ superlattice, wherein the value of x ranges from 0 to 1. In accordance with another aspect, buffer layer 32 includes an $In_yGa_{1-1}P$ superlattice, wherein the value of y ranges from 0 to 1. By varying the value of x or y, as the case may be, the lattice constant is varied from bottom to top across the superlattice to create a match between lattice constants of the underlying oxide and the overlying compound semiconductor material. The compositions of other materials, such as those listed above, may also be similarly varied to manipulate the lattice constant of layer 32 in a like manner. The superlattice can have a thickness of about 50–500 nm and preferably has a thickness of about 100–200 nm. The template for this structure can be the same of that described in example 1. Alternatively, buffer layer 32 can be a layer of monocrystalline germanium having a thickness of 1–50 nm and preferably having a thickness of about 2–20 nm. In using a germanium buffer layer, a template layer of either germanium-strontium (Ge—Sr) or germanium-titanium (Ge—Ti) having a thickness of about one monolayer can be used as a nucleating site for the subsequent growth of the monocrystalline compound semiconductor material layer. The formation of the oxide layer is capped with either a monolayer of strontium or a monolayer of titanium to act as a nucleating site for the subsequent deposition of the monocrystalline germanium. The monolayer of strontium or titanium provides a nucleating site to which the first monolayer of germanium can bond.

EXAMPLE 5

This example also illustrates materials useful in a structure 40 as illustrated in FIG. 2. Substrate material 22, accommodating buffer layer 24, monocrystalline compound semiconductor material layer 26 and template layer 30 can be the same as those described above in example 2. In addition, a buffer layer 32 is inserted between the accommodating buffer layer and the overlying monocrystalline compound semiconductor material layer. The buffer layer, a further monocrystalline semiconductor material, can be, for example, a graded layer of indium gallium arsenide (InGaAs) or indium aluminum arsenide (InAlAs). In accordance with one aspect of this embodiment, buffer layer 32 includes InGaAs, in which the indium composition varies from 0 to about 47%. The additional buffer layer 32 preferably has a thickness of about 10–30 nm. Varying the composition of the buffer layer from GaAs to InGaAs serves to provide a lattice match between the underlying monocrystalline oxide material and the overlying layer of monocrystalline compound semiconductor material. Such a buffer layer is especially advantageous if there is a lattice mismatch between accommodating buffer layer 24 and monocrystalline compound semiconductor material layer 26.

EXAMPLE 6

This example provides exemplary materials useful in structure 34, as illustrated in FIG. 3. Substrate material 22, template layer 30, and monocrystalline compound semiconductor material layer 26 may be the same as those described above in connection with example 1.

Amorphous layer 36 is an amorphous oxide layer which is suitably formed of a combination of amorphous intermediate layer materials (e.g., layer 28 materials as described above) and accommodating buffer layer materials (e.g., layer 24 materials as described above). For example, amorphous layer 36 may include a combination of $SiO_x$ and $Sr_zBa_{1-z}TiO_3$ (where z ranges from 0 to 1), which combine or mix, at least partially, during an anneal process to form amorphous oxide layer 36.

The thickness of amorphous layer 36 may vary from application to application and may depend on such factors as desired insulating properties of layer 36, type of semiconductor material comprising layer 26, and the like. In accordance with one exemplary aspect of the present embodiment, layer 36 thickness is about 2 nm to about 100 nm, preferably about 2–10 nm, and more preferably about 5–6 nm.

Layer 38 comprises a monocrystalline compound semiconductor material that can be grown epitaxially over a monocrystalline oxide material such as material used to form accommodating buffer layer 24. In accordance with one embodiment of the invention, layer 38 includes the same materials as those comprising layer 26. For example, if layer 26 includes GaAs, layer 38 also includes GaAs. However, in accordance with other embodiments of the present invention, layer 38 may include materials different from those used to form layer 26. In accordance with one exemplary embodiment of the invention, layer 38 is about 1 monolayer to about 100 nm thick.

Referring again to FIGS. 1–3, substrate 22 is a monocrystalline substrate such as a monocrystalline silicon substrate. The crystalline structure of the monocrystalline substrate is characterized by a lattice constant and by a lattice orientation. In similar manner, accommodating buffer layer 24 is also a monocrystalline material and the lattice of that monocrystalline material is characterized by a lattice constant and a crystal orientation. The lattice constants of the accommodating buffer layer and the monocrystalline substrate must be closely matched or, alternatively, must be such that upon rotation of one crystal orientation with respect to the other crystal orientation, a substantial match in lattice constants is achieved. In this context the terms "substantially equal" and "substantially matched" mean that there is sufficient similarity between the lattice constants to permit the growth of a high quality crystalline layer on the underlying layer.

Figure 4:
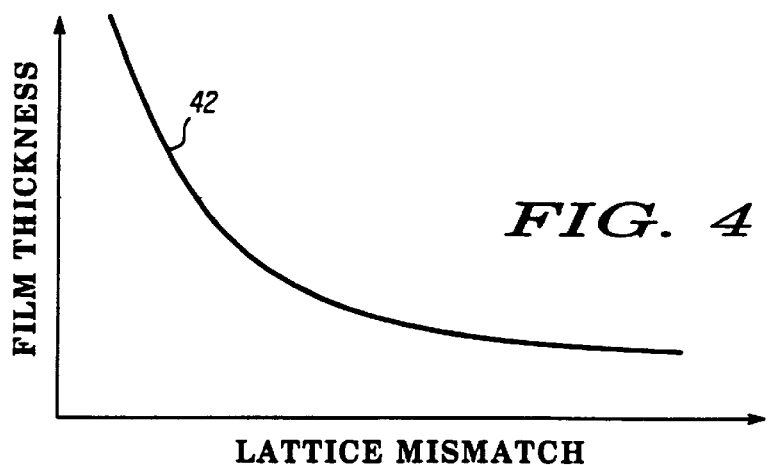
FIG. 4 illustrates graphically the relationship between maximum attainable film thickness and lattice mismatch between a host crystal and a grown crystalline overlayer.

FIG. 4 illustrates graphically the relationship of the achievable thickness of a grown crystal layer of high crystalline quality as a function of the mismatch between the lattice constants of the host crystal and the grown crystal. Curve 42 illustrates the boundary of high crystalline quality material. The area to the right of curve 42 represents layers that tend to be polycrystalline. With no lattice mismatch, it is theoretically possible to grow an infinitely thick, high quality epitaxial layer on the host crystal. As the mismatch in lattice constants increases, the thickness of achievable, high quality crystalline layer decreases rapidly. As a reference point, for example, if the lattice constants between the host crystal and the grown layer are mismatched by more than about 2%, monocrystalline epitaxial layers in excess of about 20 nm cannot be achieved.

In accordance with one embodiment of the invention, substrate 22 is a (100) or (111) oriented monocrystalline silicon wafer and accommodating buffer layer 24 is a layer of strontium barium titanate. Substantial matching of lattice constants between these two materials is achieved by rotating the crystal orientation of the titanate material by 45° with respect to the crystal orientation of the silicon substrate wafer. The inclusion in the structure of amorphous interface layer 28, a silicon oxide layer in this example, if it is of sufficient thickness, serves to reduce strain in the titanate monocrystalline layer that might result from any mismatch in the lattice constants of the host silicon wafer and the grown titanate layer. As a result, in accordance with an embodiment of the invention, a high quality, thick, monocrystalline titanate layer is achievable.

Still referring to FIGS. 1–3, layer 26 is a layer of epitaxially grown monocrystalline material and that crystalline material is also characterized by a crystal lattice constant and a crystal orientation. In accordance with one embodiment of the invention, the lattice constant of layer 26 differs from the lattice constant of substrate 22. To achieve high crystalline quality in this epitaxially grown monocrystalline layer, the accommodating buffer layer must be of high crystalline quality. In addition, in order to achieve high crystalline quality in layer 26, substantial matching between the crystal lattice constant of the host crystal, in this case, the monocrystalline accommodating buffer layer, and the grown crystal is desired. With properly selected materials this substantial matching of lattice constants is achieved as a result of rotation of the crystal orientation of the grown crystal with respect to the orientation of the host crystal. If the grown crystal is gallium arsenide, aluminum gallium arsenide, zinc selenide, or zinc sulfur selenide and the accommodating buffer layer is monocrystalline $Sr_xBa_{1-x}TiO_3$, substantial matching of crystal lattice constants of the two materials is achieved, wherein the crystal orientation of the grown layer is rotated by 45° with respect to the orientation of the host monocrystalline oxide. Similarly, if the host material is a strontium or barium zirconate or a strontium or barium hafnate or barium tin oxide and the compound semiconductor layer is indium phosphide or gallium indium arsenide or aluminum indium arsenide, substantial matching of crystal lattice constants can be achieved by rotating the orientation of the grown crystal layer by 45° with respect to the host oxide crystal. In some instances, a crystalline semiconductor buffer layer between the host oxide and the grown compound semiconductor layer can be used to reduce strain in the grown monocrystalline compound semiconductor layer that might result from small differences in lattice constants. Better crystalline quality in the grown monocrystalline compound semiconductor layer can thereby be achieved.

The following example illustrates a process, in accordance with one embodiment of the invention, for fabricating a semiconductor structure such as the structures depicted in FIGS. 1–3. The process starts by providing a monocrystalline semiconductor substrate comprising silicon or germanium. In accordance with a preferred embodiment of the invention, the semiconductor substrate is a silicon wafer having a (100) orientation. The substrate is preferably oriented on axis or, at most, about 0.5° off axis. At least a portion of the semiconductor substrate has a bare surface, although other portions of the substrate, as described below, may encompass other structures. The term "bare" in this context means that the surface in the portion of the substrate has been cleaned to remove any oxides, contaminants, or other foreign material. As is well known, bare silicon is highly reactive and readily forms a native oxide. The term "bare" is intended to encompass such a native oxide. A thin silicon oxide may also be intentionally grown on the semiconductor substrate, although such a grown oxide is not essential to the process in accordance with the invention. In order to epitaxially grow a monocrystalline oxide layer overlying the monocrystalline substrate, the native oxide layer must first be removed to expose the crystalline structure of the underlying substrate. The following process is preferably carried out by molecular beam epitaxy (MBE), although other epitaxial processes may also be used in accordance with the present invention. The native oxide can be removed by first thermally depositing a thin layer of strontium, barium, a combination of strontium and barium, or other alkaline earth metals or combinations of alkaline earth metals in an MBE apparatus. In the case where strontium is used, the substrate is then heated to a temperature of about 750° C. to cause the strontium to react with the native silicon oxide layer. The strontium serves to reduce the silicon oxide to leave a silicon oxide-free surface. The resultant surface, which exhibits an ordered 2×1 structure, includes strontium, oxygen, and silicon. The ordered 2×1 structure forms a template for the ordered growth of an overlying layer of a monocrystalline oxide. The template provides the necessary chemical and physical properties to nucleate the crystalline growth of an overlying layer.

In accordance with an alternate embodiment of the invention, the native silicon oxide can be converted and the substrate surface can be prepared for the growth of a monocrystalline oxide layer by depositing an alkaline earth metal oxide, such as strontium oxide, strontium barium oxide, or barium oxide, onto the substrate surface by MBE at a low temperature and by subsequently heating the structure to a temperature of about 750° C. At this temperature a solid state reaction takes place between the strontium oxide and the native silicon oxide causing the reduction of the native silicon oxide and leaving an ordered 2×1 structure with strontium, oxygen, and silicon remaining on the substrate surface. Again, this forms a template for the subsequent growth of an ordered monocrystalline oxide layer.

Following the removal of the silicon oxide from the surface of the substrate, in accordance with one embodiment of the invention, the substrate is cooled to a temperature in the range of about 200–800° C. and a layer of strontium titanate is grown on the template layer by molecular beam epitaxy. The MBE process is initiated by opening shutters in the MBE apparatus to expose strontium, titanium and oxygen sources. The ratio of strontium and titanium is approximately 1:1. The partial pressure of oxygen is initially set at a minimum value to grow stoichiometric strontium titanate at a growth rate of about 0.3–0.5 nm per minute. After initiating growth of the strontium titanate, the partial pressure of oxygen is increased above the initial minimum value. The overpressure of oxygen causes the growth of an amorphous silicon oxide layer at the interface between the underlying substrate and the growing strontium titanate layer. The growth of the silicon oxide layer results from the diffusion of oxygen through the growing strontium titanate layer to the interface where the oxygen reacts with silicon at the surface of the underlying substrate. The strontium titanate grows as an ordered monocrystal with the crystalline orientation rotated by 45° with respect to the ordered 2×1 crystalline structure of the underlying substrate. Strain that otherwise might exist in the strontium titanate layer because of the small mismatch in lattice constant between the silicon substrate and the growing crystal is relieved in the amorphous silicon oxide intermediate layer.

After the strontium titanate layer has been grown to the desired thickness, the monocrystalline strontium titanate is capped by a template layer that is conducive to the subsequent growth of an epitaxial layer of a desired compound semiconductor material. For the subsequent growth of a layer of gallium arsenide, the MBE growth of the strontium titanate monocrystalline layer can be capped by terminating the growth with 1–2 monolayers of titanium, 1–2 monolayers of titanium-oxygen or with 1–2 monolayers of strontium-oxygen. Following the formation of this capping layer, arsenic is deposited to form a Ti—As bond, a Ti—O—As bond or a Sr—O—As bond. Any of these form an appropriate template for deposition and formation of a gallium arsenide monocrystalline layer. Following the formation of the template, gallium is subsequently introduced to the reaction with the arsenic and gallium arsenide forms. Alternatively, gallium can be deposited on the capping layer to form a Sr—O—Ga bond, and arsenic is subsequently introduced with the gallium to form the GaAs.

Figure 5:
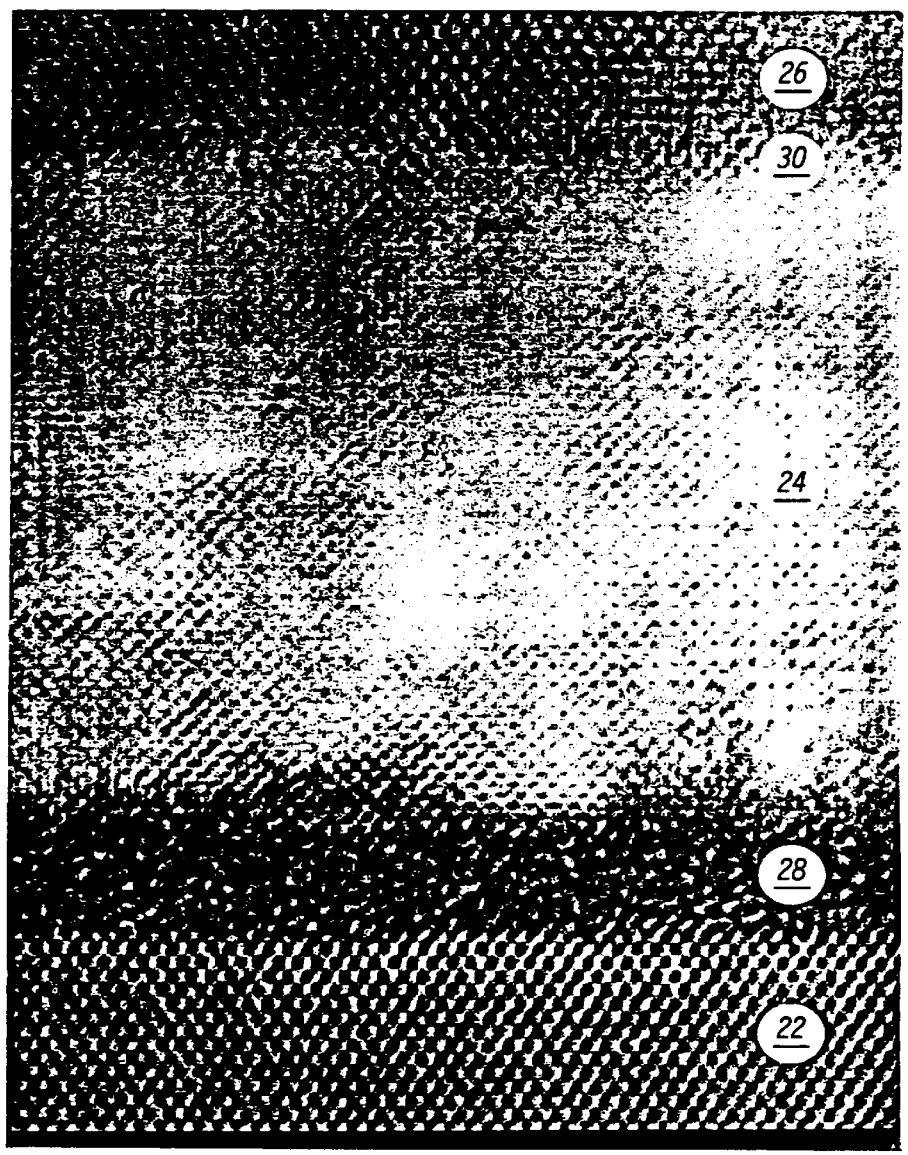
FIG. 5 illustrates a high resolution Transmission Electron Micrograph of a structure including a monocrystalline accommodating buffer layer.

FIG. 5 is a high resolution Transmission Electron Micrograph (TEM) of semiconductor material manufactured in accordance with the present invention. Single crystal SrTiO$_3$ accommodating buffer layer 24 was grown epitaxially on silicon substrate 22. During this growth process, amorphous interfacial layer 28 is formed which relieves strain due to lattice mismatch. GaAs compound semiconductor layer 26 was then grown epitaxially using template layer 30.

Figure 6:
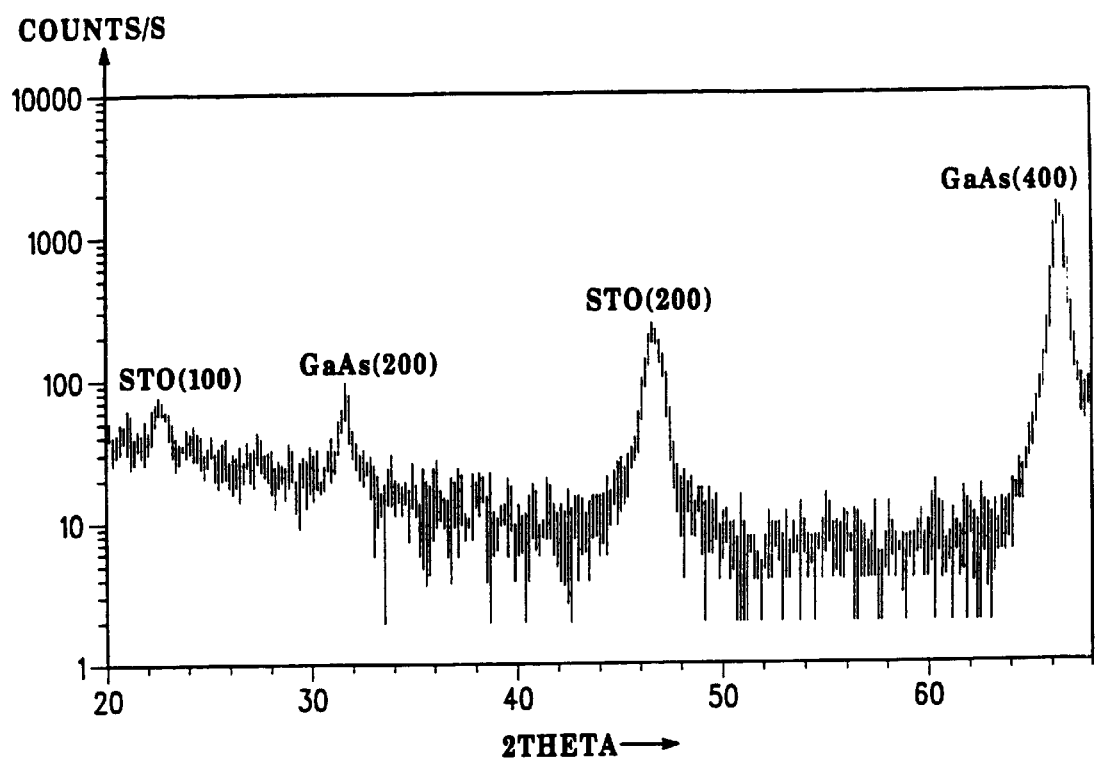
FIG. 6 illustrates an x-ray diffraction spectrum of a structure including a monocrystalline accommodating buffer layer.

FIG. 6 illustrates an x-ray diffraction spectrum taken on a structure including GaAs compound semiconductor layer 26 grown on silicon substrate 22 using accommodating buffer layer 24. The peaks in the spectrum indicate that both the accommodating buffer layer 24 and GaAs compound semiconductor layer 26 are single crystal and (100) orientated.

The structure illustrated in FIG. 2 can be formed by the process discussed with the addition of an additional buffer layer deposition step. The additional buffer layer 32 is formed overlying the template layer before the deposition of the monocrystalline compound semiconductor layer. If the buffer layer is a compound semiconductor superlattice, such a superlattice can be deposited, by MBE for example, on the template described above. If instead the buffer layer is a layer of germanium, the process above is modified to cap the strontium titanate monocrystalline layer with a final layer of either strontium or titanium and then by depositing germanium to react with the strontium or titanium. The germanium buffer layer can then be deposited directly on this template.

Structure 34, illustrated in FIG. 3, may be formed by growing an accommodating buffer layer, forming an amorphous oxide layer over substrate 22, and growing semiconductor layer 38 over the accommodating buffer layer, as described above. The accommodating buffer layer and the amorphous oxide layer are then exposed to an anneal process sufficient to change the crystalline structure of the accommodating buffer layer from monocrystalline to amorphous, thereby forming an amorphous layer such that the combination of the amorphous oxide layer and the now amorphous accommodating buffer layer form a single amorphous oxide layer 36. Layer 26 is then subsequently grown over layer 38. Alternatively, the anneal process may be carried out subsequent to growth of layer 26.

In accordance with one aspect of this embodiment, layer 36 is formed by exposing substrate 22, the accommodating buffer layer, the amorphous oxide layer, and semiconductor layer 38 to a rapid thermal anneal process with a peak temperature of about 700° C. to about 1000° C. and a process time of about 1 to about 10 minutes. However, other suitable anneal processes may be employed to convert the accommodating buffer layer to an amorphous layer in accordance with the present invention. For example, laser annealing or "conventional" thermal annealing processes (in the proper environment) may be used to form layer 36. When conventional thermal annealing is employed to form layer 36, an overpressure of one or more constituents of layer 30 may be required to prevent degradation of layer 38 during the anneal process. For example, when layer 38 includes GaAs, the anneal environment preferably includes an overpressure of arsenic to mitigate degradation of layer 38.

As noted above, layer 38 of structure 34 may include any materials suitable for either of layers 32 or 26. Accordingly, any deposition or growth methods described in connection with either layer 32 or 26, may be employed to deposit layer 38.

Figure 7:
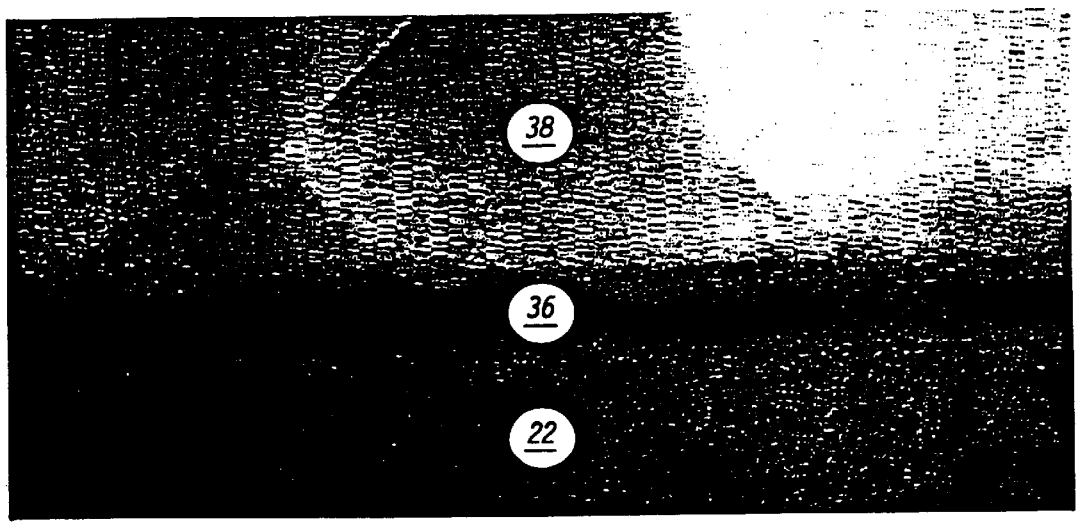
FIG. 7 illustrates a high resolution Transmission Electron Micrograph of a structure including an amorphous oxide layer.

FIG. 7 is a high resolution Transmission Electron Micrograph (TEM) of semiconductor material manufactured in accordance with the embodiment of the invention illustrated in FIG. 3. In accordance with this embodiment, a single crystal SrTiO$_3$ accommodating buffer layer was grown epitaxially on silicon substrate 22. During this growth process, an amorphous interfacial layer forms as described above. Next, GaAs layer 38 is formed above the accommodating buffer layer and the accommodating buffer layer is exposed to an anneal process to form amorphous oxide layer 36.

Figure 8:
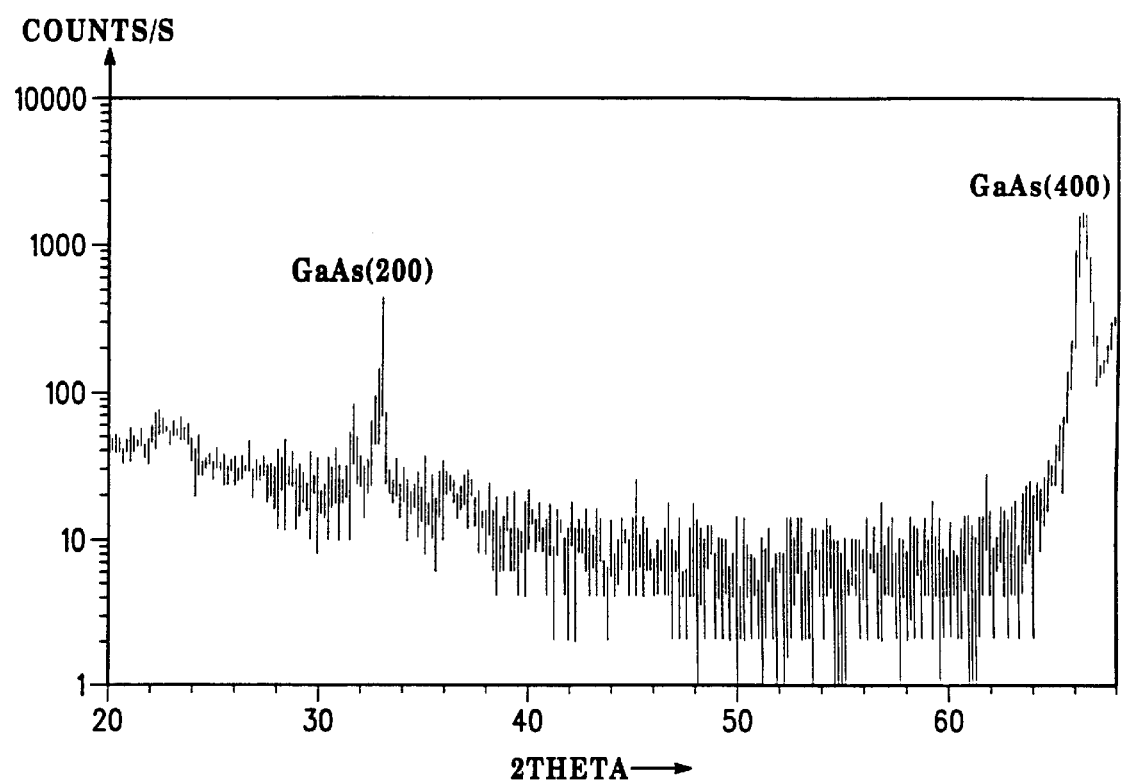
FIG. 8 illustrates an x-ray diffraction spectrum of a structure including an amorphous oxide layer.

FIG. 8 illustrates an x-ray diffraction spectrum taken on a structure including GaAs compound semiconductor layer 38 and amorphous oxide layer 36 formed on silicon substrate 22. The peaks in the spectrum indicate that GaAs compound semiconductor layer 38 is single crystal and (100) orientated and the lack of peaks around 40 to 50 degrees indicates that layer 36 is amorphous.

The process described above illustrates a process for forming a semiconductor structure including a silicon substrate, an overlying oxide layer, and a monocrystalline gallium arsenide compound semiconductor layer by the process of molecular beam epitaxy. The process can also be carried out by the process of chemical vapor deposition (CVD), metal organic chemical vapor deposition (MOCVD), migration enhanced epitaxy (MEE), atomic layer epitaxy (ALE), physical vapor deposition (PVD), chemical solution deposition (CSD), pulsed laser deposition (PLD), or the like. Further, by a similar process, other monocrystalline accommodating buffer layers such as alkaline earth metal titanates, zirconates, hafnates, tantalates, vanadates, ruthenates, and niobates, alkaline earth metal tin-based perovskites, lanthanum aluminate, lanthanum scandium oxide, and gadolinium oxide can also be grown.

Further, by a similar process such as MBE, other III–V and II–VI monocrystalline compound semiconductor layers can be deposited overlying the monocrystalline oxide accommodating buffer layer.

Each of the variations of compound semiconductor materials and monocrystalline oxide accommodating buffer layer uses an appropriate template for initiating the growth of the compound semiconductor layer. For example, if the accommodating buffer layer is an alkaline earth metal zirconate, the oxide can be capped by a thin layer of zirconium. The deposition of zirconium can be followed by the deposition of arsenic or phosphorus to react with the zirconium as a precursor to depositing indium gallium arsenide, indium aluminum arsenide, or indium phosphide respectively. Similarly, if the monocrystalline oxide accommodating buffer layer is an alkaline earth metal hafnate, the oxide layer can be capped by a thin layer of hafnium. The deposition of hafnium is followed by the deposition of arsenic or phosphorous to react with the hafnium as a precursor to the growth of an indium gallium arsenide, indium aluminum arsenide, or indium phosphide layer, respectively. In a similar manner, strontium titanate can be capped with a layer of strontium or strontium and oxygen and barium titanate can be capped with a layer of barium or barium and oxygen. Each of these depositions can be followed by the deposition of arsenic or phosphorus to react with the capping material to form a template for the deposition of a compound semiconductor material layer comprising indium gallium arsenide, indium aluminum arsenide, or indium phosphide.

Figure 9:
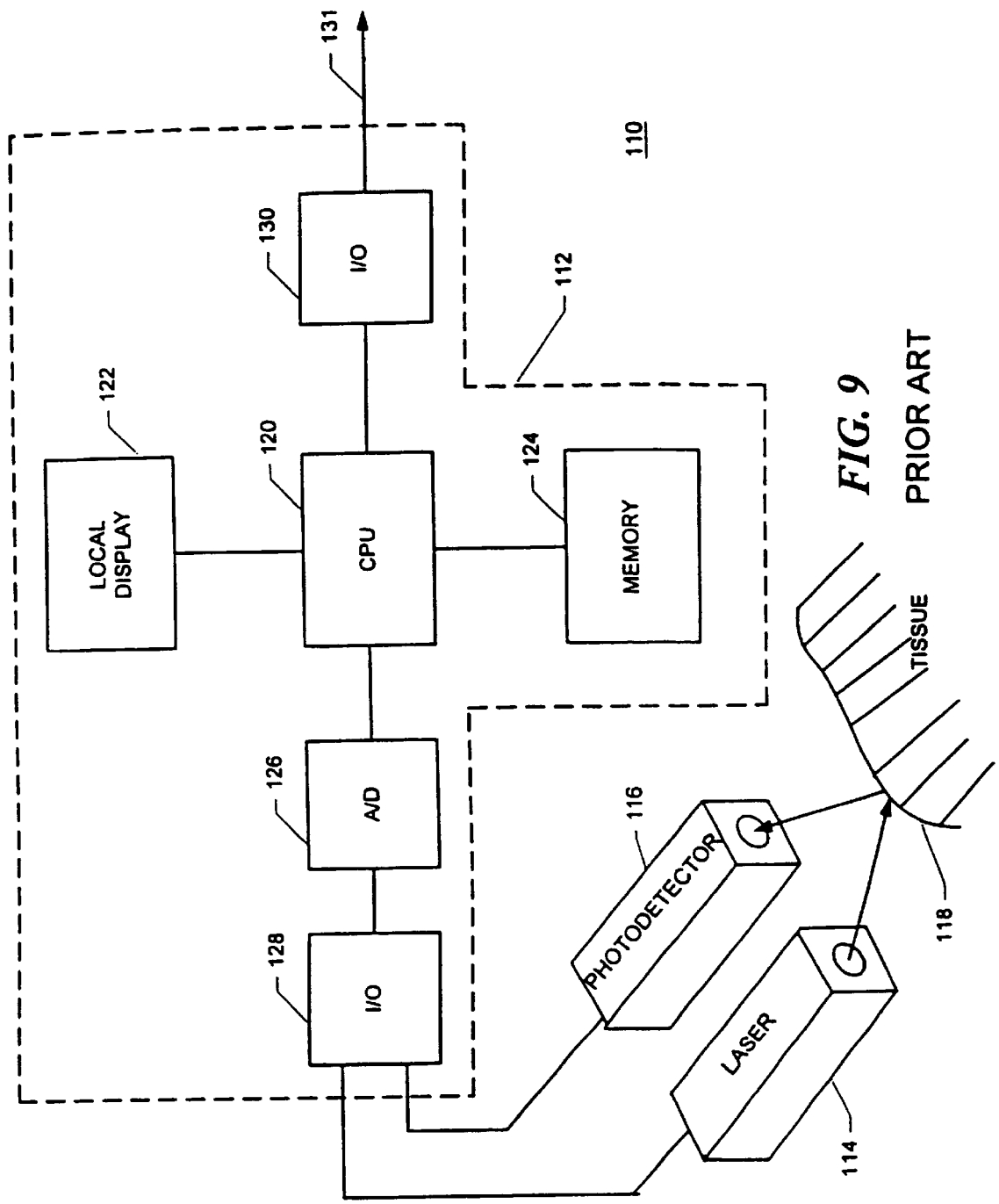
FIG. 9 is a schematic block diagram of a prior art medical diagnostic apparatus implemented in discrete components.

FIG. 9 is a schematic block diagram of a prior art medical diagnostic apparatus implemented in discrete components. In FIG. 9, a medical diagnostic system 110 includes a control unit 112, a light source such as a laser 114, and a light detector such as a photodetector 116. Light source 114 illuminates tissue 18 of an animate subject (not shown) and resultant light, such as reflectively scattered light from tissue 118, is detected by light detector 116. Control unit 112 controls activity of light source 114 and evaluates light detected by light detector 116 according to predetermined criteria.

Control unit 112 includes a processing unit such as a CPU (central processing unit) 120 coupled with a display unit 122 and a memory unit 124. Processing unit 120 communicates with an A/D (analog-to-digital) unit 126 and an I/O (input/output) unit 128 in controlling light source 114 and in receiving indication of light detections from light detector 116. Processing unit 120 cooperates with memory unit 124 and display unit 122 to store predetermined criteria for evaluating light detected by light detector 116, and to perform diagnostic evaluation of tissue 118. Such diagnostic evaluation may include, for example, blood oxygenation, hematocrit, heart rate or other diagnostic parameters associated with an animate subject.

A/D unit 126 and I/O unit 128 cooperate to ensure that signals passing among processor 120, light source 114 and light detector I 16 are compatible for each of the respective devices. A/D unit 126 and I/O unit 128 provide digital signals to digital devices, such as processor 120, provide analog signals to analog devices such as light source 114 and receive analog signals from analog devices such as light detector 116. If signals among respective components are compatible, such as in an all-digital system, then A/D unit 126 or I/O unit 128 or both units 126, 128 may be omitted from system 110 as appropriate.

Processing unit 120 is also preferably coupled with an I/O unit 130 for effecting communications to loci remote from medical diagnostic system 110. Communications with remote loci, indicated in FIG. 9 at output 131, may be effected via wires or wirelessly, and may involve any of various communication media, including RF (radio frequency) communications, optic coupling, capacitive coupling, inductive coupling, magnetic coupling, sonic coupling or other media or combination of media.

Each of the elements of control unit 112, light source 114 and light detector 116 are implemented in discrete components that are linked using wires, fiber optic cables or other connection structures. The various elements of medical diagnostic system 110 may be gathered into a single package, but the discrete nature of the components and the interconnection structures necessitated by such discrete component construction (such as additional I/O devices, extra buffer units or similar interface components; not shown in FIG. 9) ensure that any such single package will be bulky and relatively inefficient compared with a similar diagnostic system implemented according to the present invention in a monolithically fabricated integrated unitary structure.

Thus, an important structural feature emphasized in connection with the prior art apparatus illustrated in FIG. 9 is that the various devices employed in that prior art apparatus are embodied in discrete "chips", or components. The various chips are implemented in various topologies and technologies that are cost effective or otherwise appropriate for their respective operational parameters.

Accordingly, one device may be implemented in silicon, and another device may be implemented in a compound semiconductor material, such as gallium arsenide. An important point in this regard is that there are significant limitations with prior art technology in fabricating devices of such various topologies within one unitary package. Because there is no opportunity with prior art techniques for fabricating the various topologies on a single common substrate, the most "unitary" construction that a collection of several such devices may achieve is to be contained within a single enclosure, in a "unified packaging" of a plurality of chips in an attempt at a unitary structure.

Substrates employed for such unified packaging, such as alumina substrates, are oriented in a generally planar configuration upon which the various elements (i.e., devices) of the package are arrayed. Variances in the surface of such alumina substrates, measured substantially perpendicular to the plane of the substrate, are quite rough. Such roughness precludes alignment of devices to within micrometer tolerances of vertical displacement from a common plane. Such micrometer tolerances are required, for example, in crafting a unitary collection of optically communicating devices. The alternative available using rough-surfaced prior art substrates, such as alumina substrates, is to fabricate the various optical devices on separate substrates and employ fiber communications, with the attendant required I/O terminations at each end of each fiber connector. Fabricating semiconductor devices on a common substrate during the deposition or other processes used for creating the devices permits vertical placement tolerances on the order of micrometers. Such fine control of vertical placement allows ample latitude for direct optical alignment among devices on a common substrate.

Limitations in placement of devices adjacent each other are also problematic. That is, the spacing between adjacent devices, measured substantially parallel with the plane of the common substrate (e.g., alumina substrate), is limited by the accuracy of placement performed by pick-and-place machinery or similar tools used in manufacturing. As a result, the tolerance of such horizontal proximity placement is on the order of tenths of a millimeter (0.1 mm). Producing semiconductor devices on a common substrate during the deposition or other fabrication processes used for creating the devices involves horizontal placement tolerances on the order of micrometers—a difference by a factor of 100 over prior art production pick-and-place capabilities.

Being able to fabricate semiconductor devices on a common substrate during the deposition or other processes used for creating the devices permits creation of very small, compact devices. Several benefits are realized by such cohesive manufacturing techniques, including: manufacturing costs are reduced; fewer I/O devices are needed; circuit paths are shorter resulting in lower power requirements, lower radiation levels and less electromagnetic noise generation; fewer circuit elements liable to fail means that reliability is increased. Monolithic construction attainable with such unitary structures is more easily sealed against environmental influences. The benefits of such an improved semiconductor manufacturing capability at the fabrication (deposition or other process) level are especially significant in optical systems because various optical elements may be aligned within photolithographical tolerances—on the order of micrometers—to ensure alignment of optical elements such as waveguides, lasers, fibers and other elements. Connecting fibers and I/O terminations intermediate various optical elements, and their associated losses and other inefficiencies, are thereby eliminated.

Medical diagnostic apparatuses constructed in such a process-level unified construction are better aligned, more compact, more reliable and robust, better protectable against environmental influences (including electromagnetic noise), and generally more versatile and convenient in their employability for particular applications because of their lower power requirements and smaller size.

Figure 10:
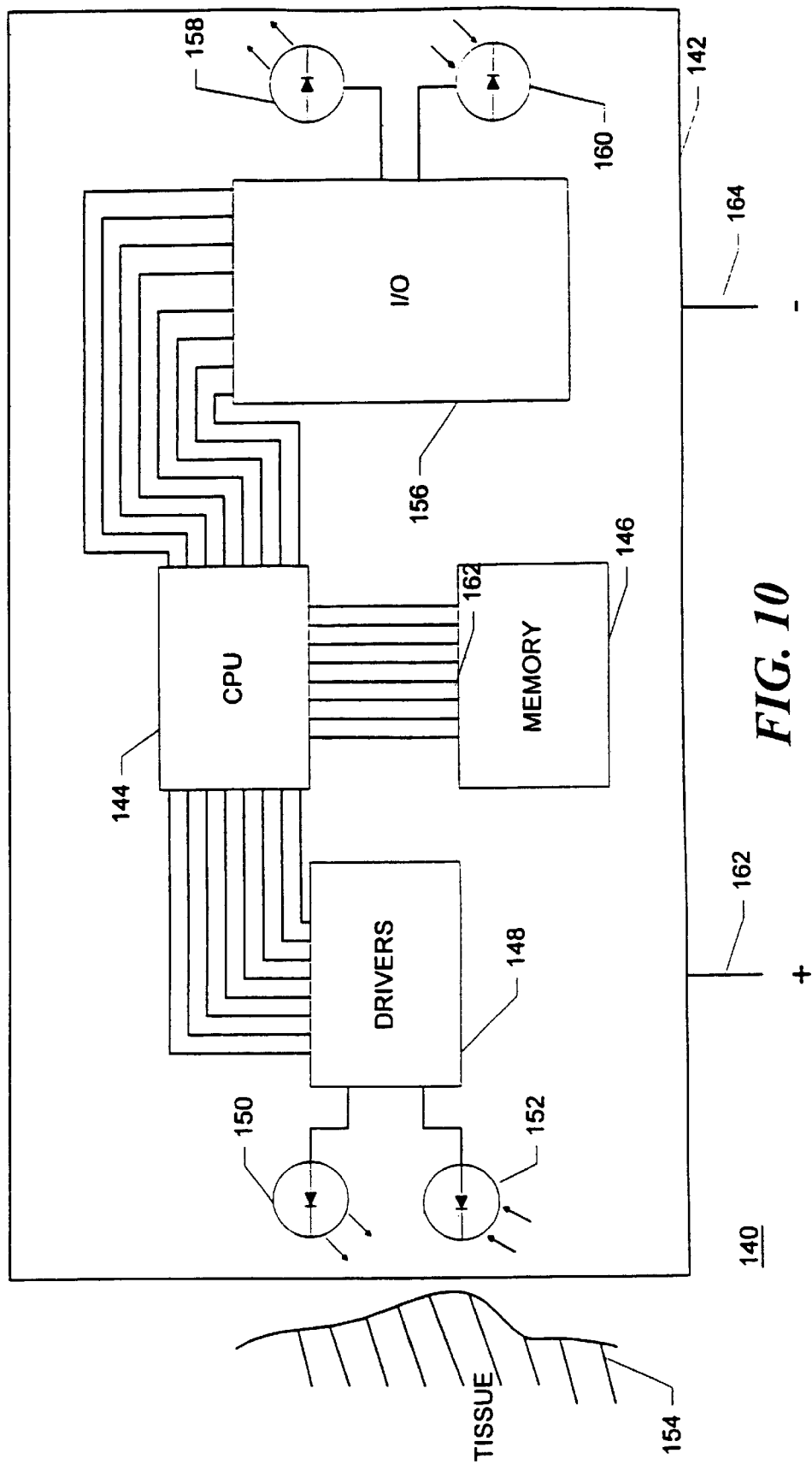
FIG. 10 is a schematic block diagram in plan view of a medical diagnostic apparatus constructed according to the teachings of the present invention.

FIG. 10 is a schematic block diagram in plan view of a medical diagnostic apparatus constructed according to the teachings of the present invention. In FIG. 10, a medical diagnostic system 140 is monolithically fabricated in a unitary structure upon a common substrate 142. Preferably, common substrate 142 is a silicon substrate. Medical diagnostic system 140 includes a processing unit such as a CPU (central processing unit) 144 with an associated memory unit 146. Processing unit 144 communicates with drivers 148 for controlling optic elements 150, 152. Preferably one optic element, such as optic element 150, is a light source such as a laser for illuminating tissue 154 of an animate subject (not shown), and the other optic element 152 is a light detector for receiving resultant light from tissue 154. Resultant light may be in the form of reflected scattered light when optic elements 150, 152 are situated on the same side of tissue 154. Alternatively, resultant light may be refracted and scattered light transmitted through tissue 154 when optic elements 150, 152 are situated on opposing sides of tissue 154.

Processing unit 144 also communicates with an I/O (input/output) unit 156 for controlling optic communications using optic elements 158, 160. Medical diagnostic system 140 is illustrated in a representative embodiment configured for optically coupled communication of diagnostic information to a locus remote from system 140. Preferably one optic element, such as optic element 158, is a light source such as a laser for optically communicating information to a remote locus (not shown), and the other optic element 160 is an optical communication receiver for receiving optically coupled communications from a remote locus. Power supply terminals 162,164 provide accessibility for providing power to system 140.

Other communication media could be incorporated into system 140 either in lieu of optical communications, or in addition to optical communications, and implemented into system 140 in a fabrication level integrated unitary structure.

A salient feature of system 140 is the unitary construction employed in its fabrication. Respective elements of medical diagnostic system 140 are illustrated in FIG. 10 as physically displaced in order to facilitate understanding of the invention. In its preferred embodiment, respective elements of medical diagnostic system 140 are compactly arrayed upon substrate 142 according to the teachings of the present invention. Individual elements of medical diagnostic system 140 in FIG. 10 are substantially similar to selected elements of system 110 (FIG. 9). For example, optical element 150 (FIG. 10) may light source 114 (FIG. 9). A significant difference between system 110 FIG. 9) and system 140 (FIG. 10) is that the elements of system 140 are monolithically fabricated upon a common substrate (preferably a silicon substrate). This feature of medical diagnostic system 140 is illustrated in FIG. 11.

Figure 11:
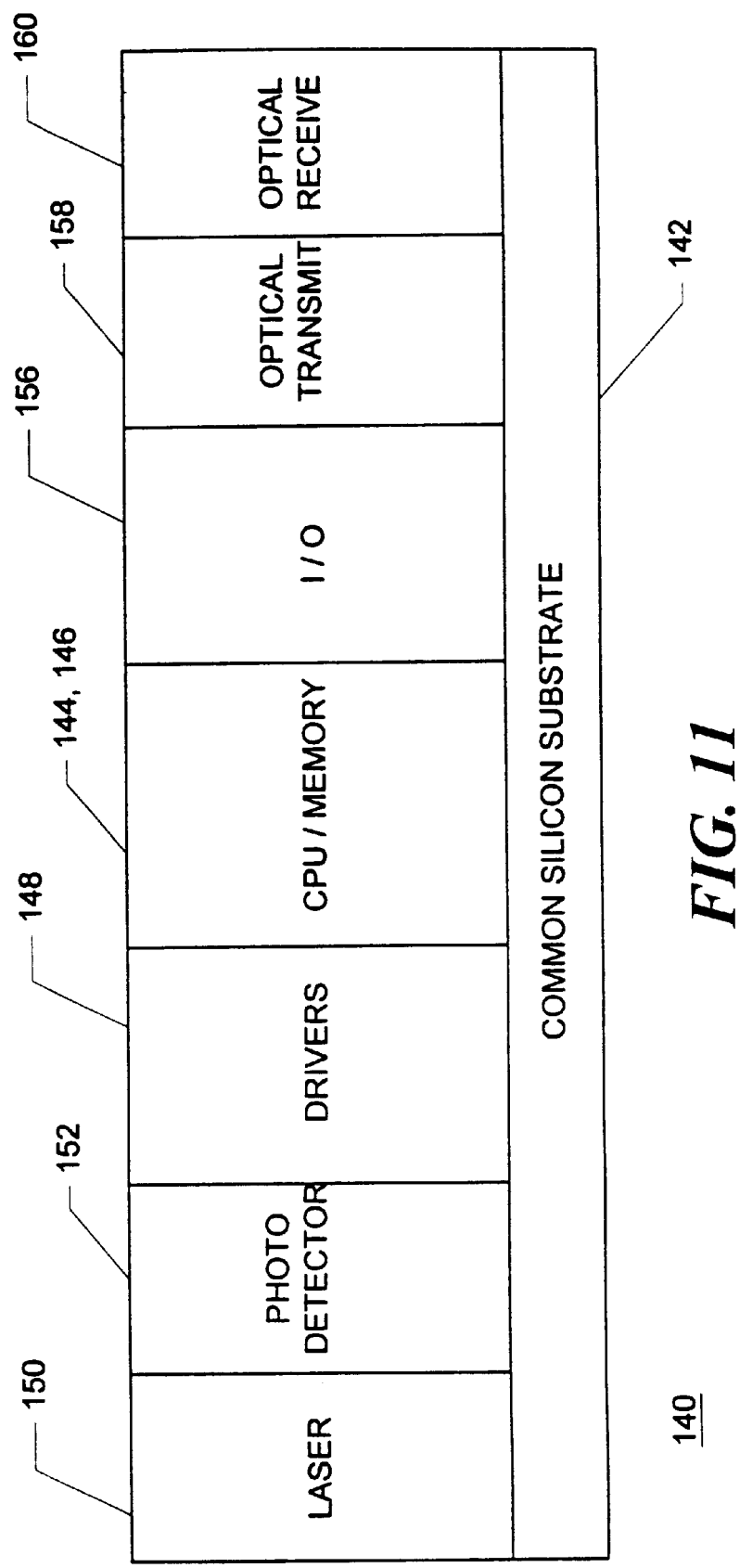
FIG. 11 is a schematic block diagram in elevation view of the medical apparatus constructed according to the teachings of the present invention illustrated in FIG. 10.

FIG. 11 is a schematic block diagram in elevation view of the medical apparatus constructed according to the teachings of the present invention illustrated in FIG. 10. In FIG. 11, medical diagnostic system 140 is comprised of a plurality of elements arrayed upon a common silicon substrate 142. The elements are preferably monolithically fabricated as a unitary structure. Thus, optic element/laser 150, optic element/photodetector 152, drivers 148, processor 144, memory 146 (processor 144 and memory 146 are illustrated as being constructed in their preferred embodiment as a single integral structure), I/O unit 156, optical element/optical transmitter 158 and optical element/optical receiver 160 are substantially intimately situated and connected upon substrate 142.

Figure 12:
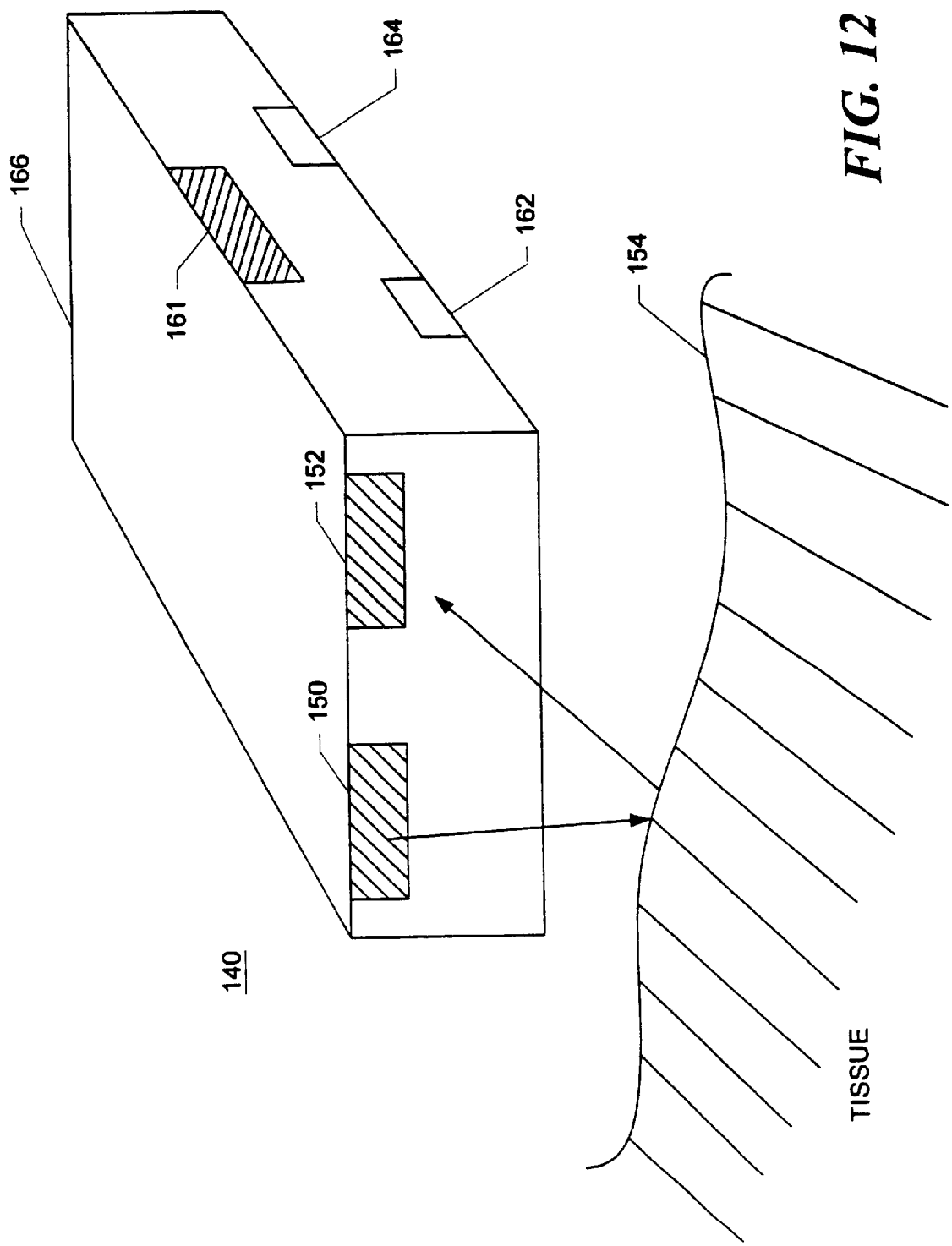
FIG. 12 is a perspective illustration of a representative medical diagnostic product including the apparatus described in connection with FIGS. 10 and 11.

FIG. 12 is a perspective illustration of a representative medical diagnostic product including the apparatus described in connection with FIGS. 10 and 11. In FIG. 12, medical diagnostic system 140 is contained as a unitary structure within an enclosure 166; as a result, only some aspects of diagnostic system 140 are visible in FIG. 12. Enclosure 166 provides power supply access nodes 162, 164 for providing power to system 140 from outside enclosure 166, as by a battery or other power source (not shown). Optic element/light source 150 is accessible from outside enclosure 166 for illuminating tissue 154. Optic element/light detector 152 is accessible from outside enclosure 166 for receiving resultant light from tissue 154. Optical elements 158, 160 (not shown in FIG. 12) are accessible from outside enclosure 166 as by an optical communication access aperture 161.

Figure 13:
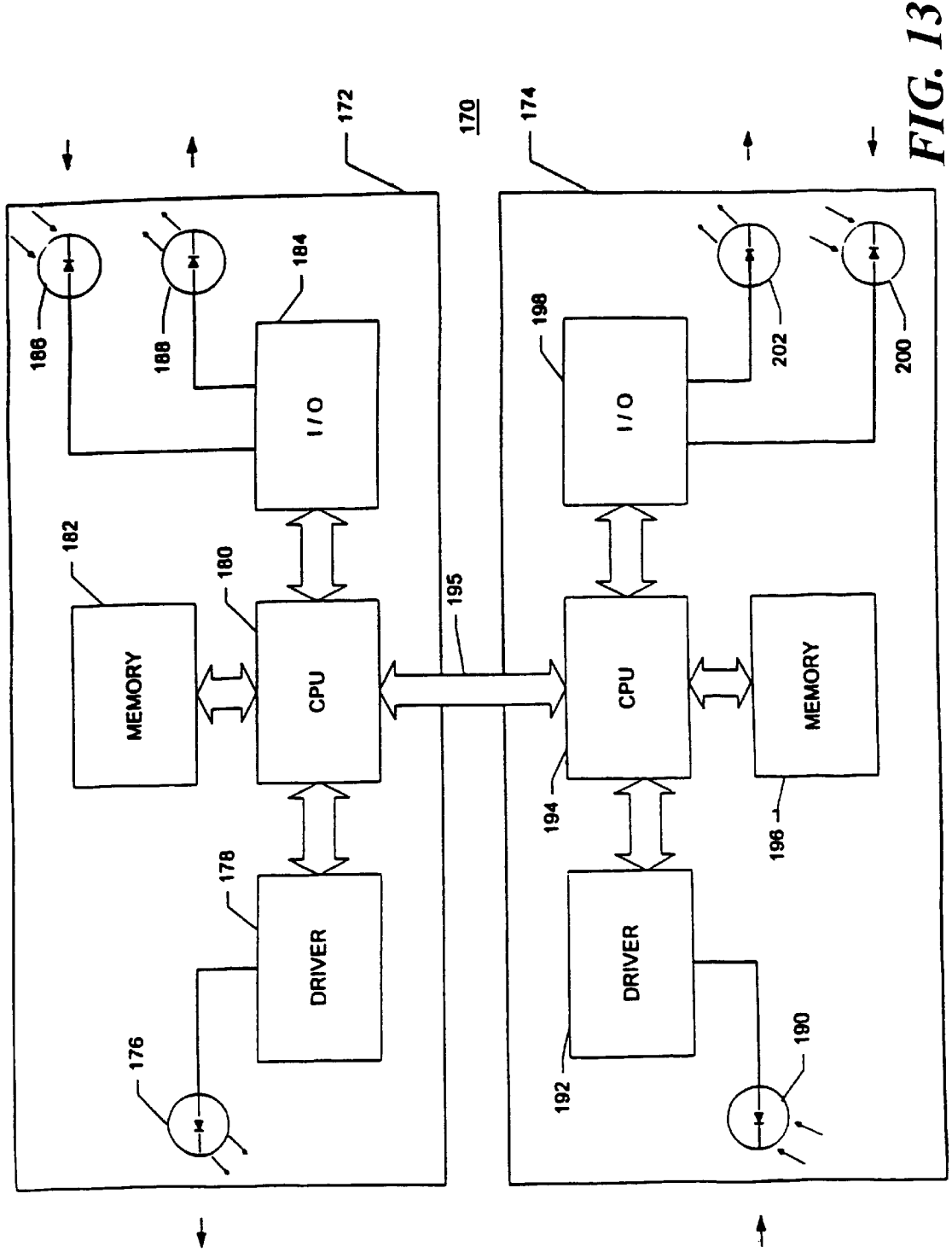
FIG. 13 is a schematic block diagram illustrating an alternate embodiment of a medical diagnostic apparatus constructed according to the teachings of the present invention.

FIG. 13 is a schematic block diagram illustrating an alternate embodiment of a medical diagnostic apparatus constructed according to the teachings of the present invention. In FIG. 13, a medical diagnostic system 170 is embodied in two similar subsystems 172, 174. Subsystem 172 includes an optic element 176, a driver circuit 178 coupled with optic element 176 for driving optic element 176 in response to commands from a processor 180. Processor 180 is preferably embodied in a central a processing unit (CPU) and has an associated memory unit 182. Memory unit 182 and processor 180 may be integrally formed. Processor 180 is coupled with an I/O (input/output) unit 184 for operating optic elements 186, 188. Optic element 176 is configured as a light source, optic element 186 is configured as an optical communication receiver and optic element 188 is configured as an optical communication transmitter.

Subsystem 174 includes an optic element 190, a driver circuit 192 coupled with optic element 190 for driving optic element 190 in response to commands from a processor 194. Processor 194 is preferably embodied in a central processing unit (CPU) and has an associated memory unit 196. Memory unit 196 and processor 194 may be integrally formed. Processor 194 is coupled with an I/O (input/output) unit 198 for operating optic elements 200, 202. Optic element 190 is configured as a light detector, optic element 200 is configured as an optical communication receiver and optic element 202 is configured as an optical communication transmitter. Processors 180, 194 may be configured to communicate and cooperate with each other, as indicated by a two-way arrow 195.

The embodiment of the present invention illustrated in FIG. 13 is preferably embodied in a unitary monolithic structure similar to the structure illustrated and described in connection with FIG. 11 and is suited for employment in a product such as the product illustrated in FIG. 14 for detecting resultant light transmitted through tissue.

Figure 14:
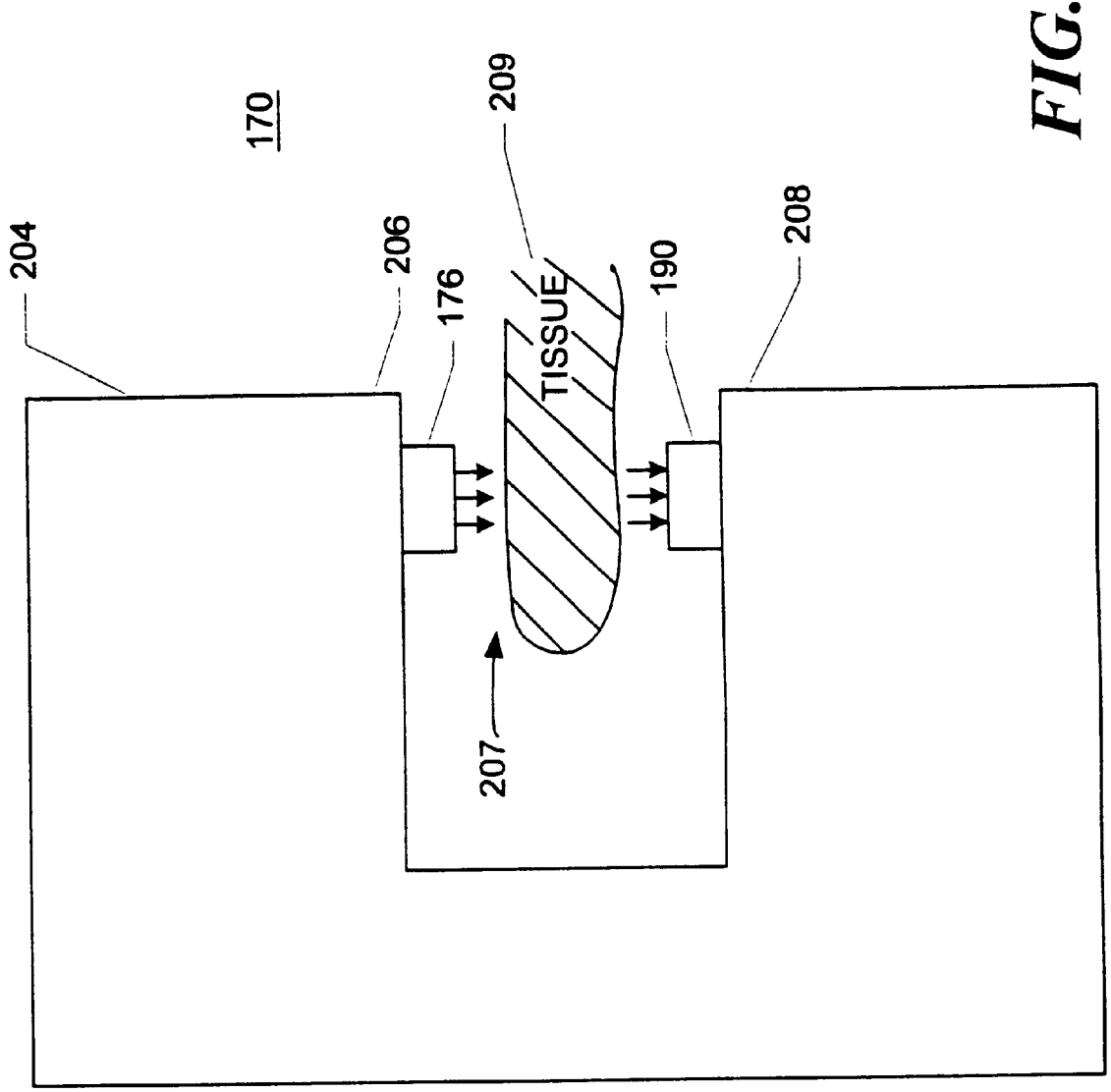
FIG. 14 is a side elevation view of a representative medical diagnostic product including the apparatus described in connection with FIG. 13.

FIG. 14 is a side elevation view of a representative medical diagnostic product including the apparatus described in connection with FIG. 13. In FIG. 14, medical diagnostic system 170 (FIG. 13) is contained as a unitary structure within an enclosure 204; as a result, only some aspects of diagnostic system 170 are visible in FIG. 14.

Enclosure 204 has opposing stations 206, 208 presenting optic element/light source 176 and optic element/light detector 190 in facing relation. A space 207 between optic element/light source 176 and optic element/light detector 190 accommodates an interposed tissue 209. In such an arrangement, with tissue 209 inserted into space 207 intermediate optic element/light source 176 and optic element/light detector 190, resultant light from optic element/light source 176 that traverses tissue 209 is received by optic element/light detector 190. The received resultant light is provided to processor 194 (FIG. 13). Processor 194, perhaps in cooperation with processor 180, evaluates the received resultant light according to predetermined criteria and results are sent to a remote locus via optic element/optical communication transmitter 200. If processors 180, 194 are in communication, then only one set of optical communication elements may be required to implement system 170. Thus, in such an alternate embodiment, optical elements 188, 200 may be eliminated so that all transmissions from system 170 to remote loci may be handled by optic element/optical communication transmitter 202, and all receptions of communications by system 170 may be handled by optical element/optical communication receiver 186. Other communication media may be employed in addition to, or instead of, optical communications. Other alternate configurations may also be employed that are within the skill of one skilled in the relevant art, and are not recited here in order to avoid prolixity. By way of example, one alternate embodiment may provide that stations 206, 208 may be hingedly joined to permit easier placement of tissue 209 within space 207 and result in closer proximity of stations 206, 208 with tissue 209 during diagnostic evaluations.

Figure 15:
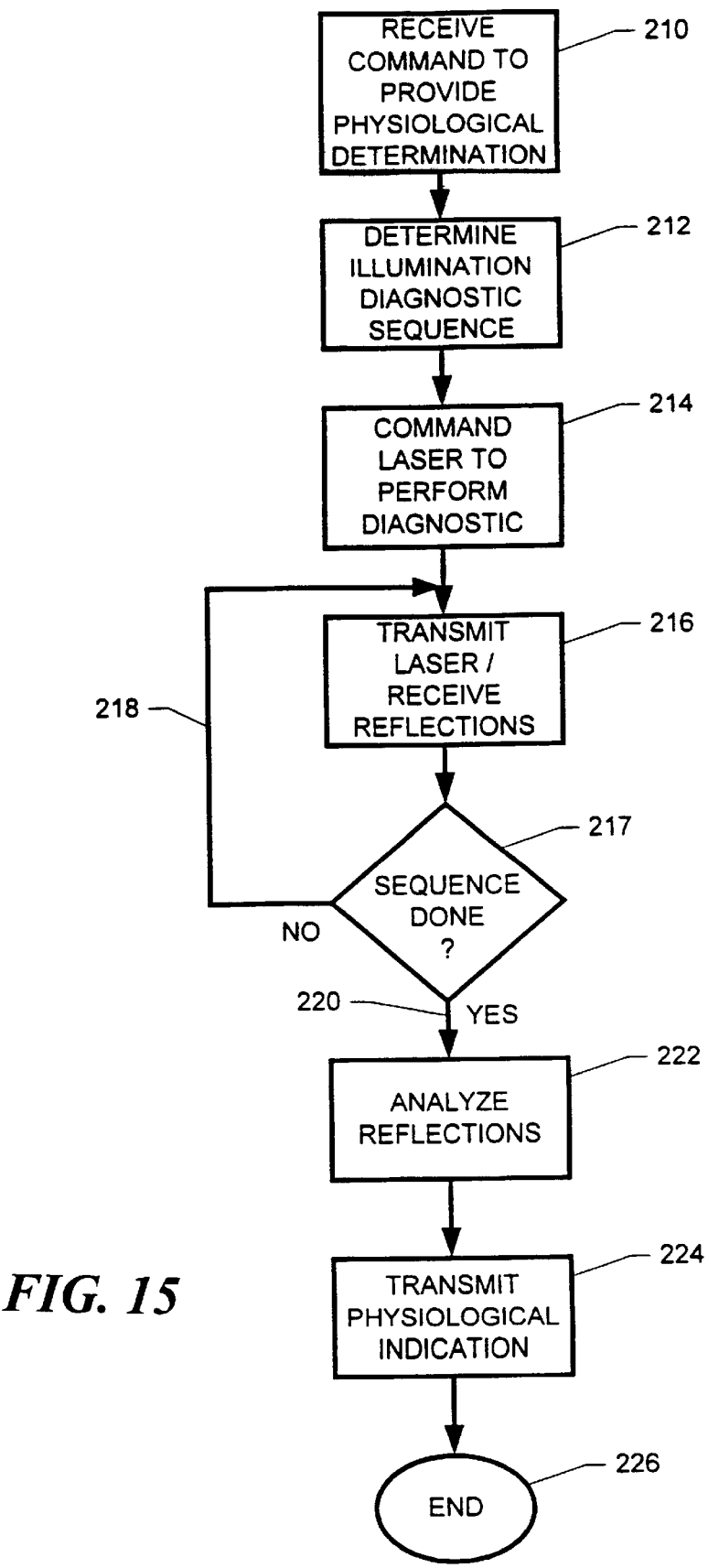
FIG. 15 is a flow chart illustrating a first embodiment of the method of the present invention.

FIG. 15 is a flow chart illustrating a first embodiment of the method of the present invention. In FIG. 15, a method for measuring at least one selected physical condition of an animate subject is carried out using an apparatus configured according to the teachings of the present invention. In FIG. 15 the method is performed in response to an externally generated command and begins with receiving the command to provide the required physiological determination, as indicated by a block 210. The method continues by determining an appropriate illumination diagnostic sequence, as indicated by a block 212. This step relates to selecting an appropriate illumination sequence to be effected by the light source (e.g., laser) for the desired physiological determination. If the method/apparatus is only intended to perform a particular measurement, this step (block 212) may be omitted because the required illumination sequence will not be selectable; it will be permanently set as the sequence to be effected.

The method continues by commanding the laser to perform the diagnostic sequence determined according to block 212, as indicated by a block 214. The laser is preferably an on-board laser unitarily fabricated in a monolithic structure according to the teachings of the present invention.

For example, the apparatus and method of the present invention may provide for fabricating a laser and a photodiode in proximity to each other. In such an embodiment VCSEL (vertical cavity surface emitting laser) technology may be grown on a silicon layer, and an adjacent photodiode may be fabricated on the same common silicon substrate in an appropriate material sensitive to the wavelength emitted by the laser. Horizontally (i.e., substantially parallel to the plane of the common substrate) emitting laser structures may be employed using the teachings of the present invention with equal advantage.

The laser then transmits the appropriate diagnostic light pattern, and the resultant light is received by a light detector, as indicated by a block 216.

A query is next posed: "Is the Sequence Done?", as indicated by a query block 217. The query is to ascertain whether the complete diagnostic sequence determined according to block 212 has been transmitted according to block 216. If the sequence is not done, then the method continues via "NO" response path 218 and transmission by the light source/laser continues according to block 216. If the diagnostic sequence is done, then the method proceeds according to "YES" response path 220 and the reflections (or other resultant light, depending upon the physical set-up in which the associated apparatus is employed) are analyzed by a processor according to predetermined criteria (e.g., processor/memory 144, 146; FIG. 10), as indicated by a block 222.

The method continues by transmitting test results in the form of physiological indications consistent with the determination ordered (block 210), as indicated by a block 224. In this embodiment of the method of the present invention—responding to a command for effecting a diagnostic determination—ends after the diagnostic determination is made and the results are transmitted, as indicated by "END" block 224. The method awaits reception of a new command (block 210) for restarting.

Figure 16:
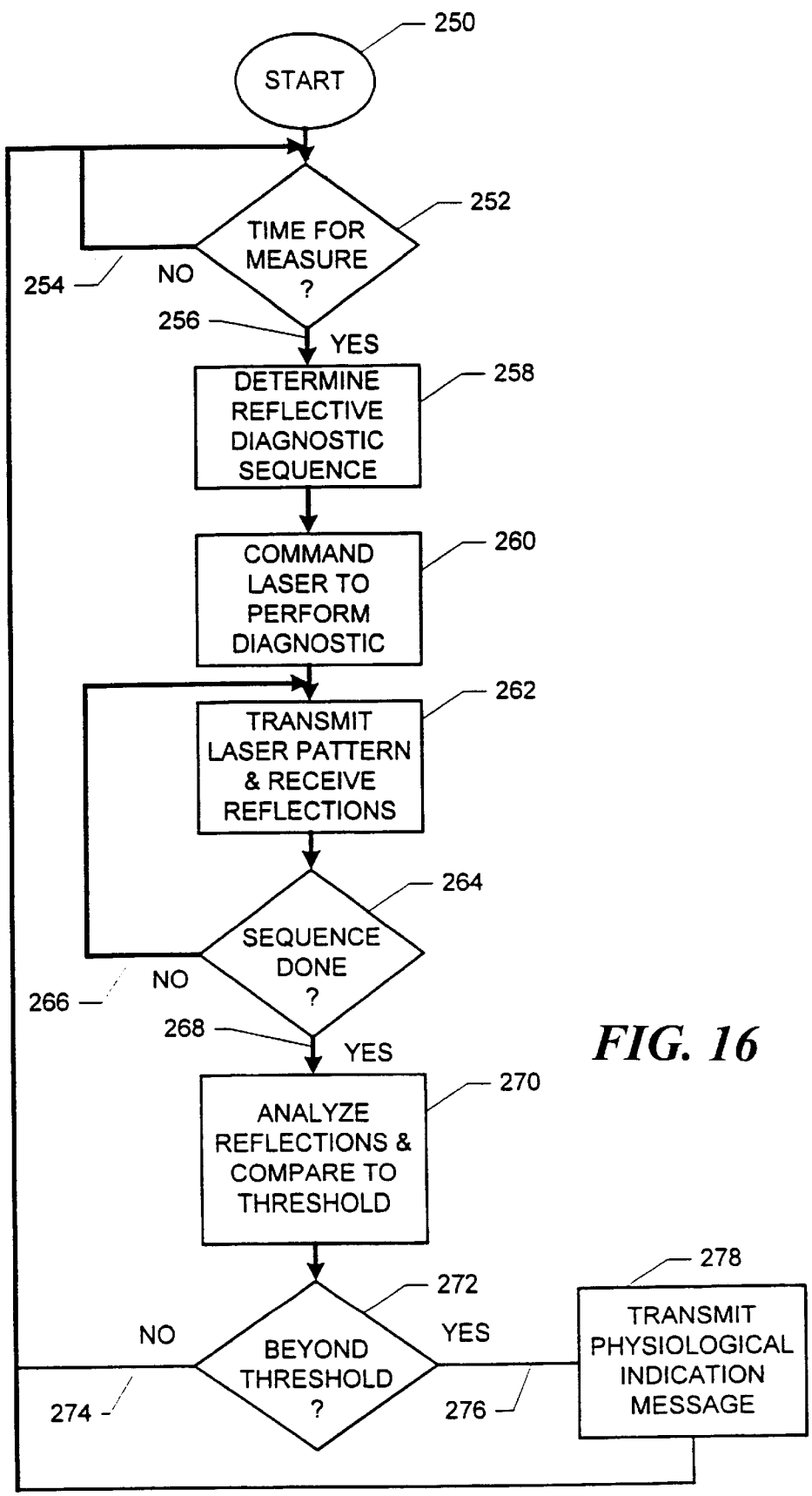
FIG. 16 is a flow chart illustrating a second embodiment of the method of the present invention.

FIG. 16 is a flow chart illustrating a second embodiment of the method of the present invention. In FIG. 16, a method for measuring at least one selected physical condition of an animate subject is carried out using an apparatus configured according to the teachings of the present invention in a monitoring mode. In FIG. 16 the method relates to a monitoring mode of execution in which the method is performed periodically according to a predetermined schedule or in response to a predetermined stimulus. The method begins with a "START" block 250 and proceeds to a query block 252 to determine whether it is time to measure the parameter for which the method is designed. If it is not time to perform a measurement, the method proceeds according to "NO" response line 254 and query is again made according to query block 252. Query block 252 could just as well inquire whether a predetermined stimulus or other event has occurred as a measure of whether the method should continue.

If it is time to perform a measurement, the method proceeds according to "YES" response line 256 and continues by determining an appropriate illumination diagnostic sequence, as indicated by a block 258. This step relates to selecting an appropriate illumination sequence to be effected by the light source (e.g., laser) for the desired physiological determination. If the method/apparatus is only intended to perform a particular measurement, this step (block 258) may be omitted because the required illumination sequence will not be selectable; it will be permanently set as the sequence to be effected.

The method continues by commanding the laser to perform the diagnostic sequence determined according to block 258, as indicated by a block 260. The laser is preferably an on-board laser unitarily fabricated in a monolithic structure according to the teachings of the present invention.

For example, the apparatus and method of the present invention may provide for fabricating a laser and a photodiode in proximity to each other. In such an embodiment VCSEL (vertical cavity surface emitting laser) technology may be grown on a silicon layer, and an adjacent photodiode may be fabricated on the same common silicon substrate in an appropriate material sensitive to the wavelength emitted by the laser. Horizontally (i.e., substantially parallel to the plane of the common substrate) emitting laser structures may be employed using the teachings of the present invention with equal advantage.

The laser then transmits the appropriate diagnostic light pattern, and the resultant light is received by a light detector, as indicated by a block 262.

A query is next posed: "Is the Sequence Done?", as indicated by a query block 264. The query is to ascertain whether the complete diagnostic sequence determined according to block 258 has been transmitted according to block 262. If the sequence is not done, then the method continues via "NO" response path 266 and transmission by the light source/laser continues according to block 262. If the diagnostic sequence is done, then the method proceeds according to "YES" response path 268 and the reflections (or other resultant light, depending upon the physical set-up in which the associated apparatus is employed) are analyzed by a processor according to predetermined criteria (e.g., processor/memory 144, 146; FIG. 10), as indicated by a block 270. The analysis in this monitoring embodiment of the method of the present invention may preferably comprise comparing resultant light received with a predetermined threshold value, or a plurality of predetermined threshold values. Another analysis may be to determine whether certain predetermined conditions are met that are not in the nature of a threshold but may nevertheless be identified as satisfied or not.

The method next poses a query: "Is the Detected Value Beyond the Threshold?", as indicated by a query block 272. This query is to test the analysis of the received resultant light with the predetermined criteria performed according to block 270 in order to ascertain whether notification to a remote locus, or recording in a recording medium, or some other responsive action is required according to predetermined monitoring arrangements. Query block 272 could just as well inquire whether certain predetermined conditions are met, or inquire as to satisfaction of some other test criteria.

If the detected resultant light does not meet predetermined criteria, then the method proceeds according to "NO" response path 274 and the method returns to query block 252 to await the next occasion for a monitoring sequence. If the detected resultant light meets predetermined criteria, then the method proceeds according to "YES" response path 276 and a physiological indication according to the determination monitored is transmitted, as indicated by a block 278. Block 278 may occasion other responsive actions if desired, such as recording the event in a memory for later retrieval, either in addition to effecting communications or instead of effecting communications.

The method continues by returning from block 278 to query block 252 to await the next occasion for a monitoring sequence.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential features or elements of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

We claim:

1. An apparatus for measuring at least one selected physical condition of an animate subject, the apparatus comprising:
   a light source;
   a light receiver, said light receiver capable of receiving resultant light from said light source via said subject; and
   an information processor connected with at least said light receiver; said information processor receiving an indication of said resultant light from said light receiver and evaluating said indication to effect said measuring,
   said information processor being implemented in a unitary structure with at least one of said light source and said light detector; said unitary structure comprising
      a monocrystalline silicon substrate;
      a monocrystalline perovskite oxide material overlying at least a portion of the monocrystalline silicon substrate;
      an amorphous oxide material located between the monocrystalline perovskite oxide material and the monocrystalline silicon substrate; and
      a monocrystalline compound semiconductor material overlying at least a portion of the monocrystalline perovskite oxide material,
   wherein at least a portion of said information processor is formed within the monocrystalline silicon substrate and at least a portion of said light source is formed within the compound semiconductor material.

2. An apparatus for measuring at least one selected physical condition of an animate subject as recited in claim 1 wherein the apparatus further comprises at least one first interface element coupled with said processor and with at least said light receiver; said at least one first interface element facilitating communication with said processor; said at least one first interface element being implemented in said unitary structure.

3. An apparatus for measuring at least one selected physical condition of an animate subject as recited in claim 1 or 2 wherein the apparatus further comprises at least one second interface element coupled with said processor; said at least one second interface element including communication means for conveying messages to loci remote from the apparatus; said at least one second interface element being implemented in said unitary structure.

4. An apparatus for measuring at least one selected physical condition of an animate subject as recited in claim 3 wherein said conveying is effected using optically coupled communications.

5. An apparatus for measuring at least one selected physical condition of an animate subject as recited in claim 3 wherein said conveying is effected using radio frequency communications.

6. An apparatus for measuring at least one selected physical condition of an animate subject as recited in claim 3 wherein said conveying is effected using sonically coupled communications.

7. An apparatus for measuring at least one selected physical condition of an animate subject as recited in claim 3 wherein said conveying is effected using magnetically coupled communications.

8. An apparatus for measuring at least one selected physical condition of an animate subject as recited in claim 3 wherein said conveying is effected using inductively coupled communications.

9. An apparatus for measuring at least one selected physical condition of an animate subject as recited in claim 3 wherein said conveying is effected using capacitively coupled communications.

10. An apparatus for measuring at least one selected physical condition of an animate subject as recited in claim 1 or 2 wherein the apparatus is arranged with said light source and said light receiver in a substantially facing orientation; said light receiver receiving said resultant light having traversed said subject.

11. An apparatus for measuring at least one selected physical condition of an animate subject as recited in claim 1 or 2 wherein the apparatus is arranged with said light source and said light receiver in a substantially adjacent orientation; said light receiver receiving said resultant light having been reflectively scattered by said subject.

12. An apparatus for measuring at least one selected physical condition of an animate subject as recited in claim 1 or 2 wherein the apparatus comprises means for monitoring said subject for an extended period of time.

13. An apparatus for measuring at least one selected physical condition of an animate subject as recited in claim 12 wherein the apparatus is configured as a clothing accessory.

14. The integrated circuit according to claim 1, wherein the monocrystalline perovskite oxide material is rotated with respect to the monocrystalline silicon layer such that the effective lattice mismatch between the monocrystalline perovskite material and the monocrystalline silicon layer is no greater than about 2.0%.

15. The integrated circuit according to claim 1, wherein the monocrystalline compound semiconductor material is rotated with respect to the monocrystalline perovskite oxide material such that the effective lattice mismatch between the monocrystalline compound semiconductor material and the monocrystalline perovskite oxide material is no greater than about 2.0%.

16. The integrated circuit according to claim 1, wherein the amorphous layer is prepared by a process comprising exposing the monocrystalline silicon substrate to the elements of the monocrystalline perovskite material while varying the partial pressure of oxygen to both 1) epitaxially grow the perovskite layer, and 2) form an amorphous silicon oxide layer overlying the silicon substrate.

17. The integrated circuit according to claim 1, wherein the monocrystalline silicon substrate is oriented in the (100) direction.

18. The integrated circuit according to claim 1, wherein the amorphous material includes oxygen and silicon.

19. The integrated circuit according to claim 1, wherein the amorphous oxide material is approximately 0.5 to 5 nanometers thick.

20. The integrated circuit according to claim 1, wherein the amorphous oxide material is approximately 1.5 to 2.5 nanometers thick.

21. The integrated circuit according to claim 1, wherein the monocrystalline perovskite oxide material is $Sr_zBa_{1-z}TiO_3$, wherein z ranges from 0 to 1.

22. The integrated circuit according to claim 1, wherein the monocrystalline compound semiconductor material includes gallium and arsenic.

23. The integrated circuit according to claim 1, wherein the monocrystalline perovskite oxide is strontium titanate, the amorphous layer includes silicon and oxygen, and the monocrystalline compound semiconductor material includes gallium and arsenic.

24. An apparatus for measuring at least one hematologic condition of an animate subject; the apparatus comprising:
   a laser device;
   a light detector device, said light detector device capable of detecting resultant light from said laser device via said subject;
   a processor device connected with said laser device and with said light detector device; said processor device receiving at least one indication of said resultant light from said light detector device and evaluating said at least one indication according to predetermined parameters to effect said measuring; and
   an information handling device coupled with said processor device; said information handling device cooperating with said processor device to convey at least one selected indication of the at least one indication,
   said processor device being implemented in a unitary structure with said information handling device and with at least one of said laser device and said light detector device; said unitary structure comprising
      a monocrystalline silicon substrate;
      a monocrystalline perovskite oxide material overlying at least a portion of the monocrystalline silicon substrate;
      an amorphous oxide material located between the monocrystalline perovskite oxide material and the monocrystalline silicon substrate; and
      a monocrystalline compound semiconductor material overlying at least a portion of the monocrystalline perovskite oxide material,
wherein at least a portion of said processor device is formed within the monocrystalline silicon substrate and at least a portion of said laser is formed within the monocrystalline compound semiconductor material.

25. An apparatus for measuring at least one hematologic condition of an animate subject as recited in claim 24 wherein said information handling device includes a memory device; said memory device storing said at least one selected indication; said memory device capable of being being queried for periodic access to the at least one selected indication.

26. An apparatus for measuring at least one hematologic condition of an animate subject as recited in claim 24 or 25 wherein said information handling device includes a communication device; said communication device periodically conveying the at least one selected indication.

27. An apparatus for measuring at least one hematologic condition of an animate subject as recited in claim 26 wherein said conveying is effected using optically coupled communications.

28. An apparatus for measuring at least one hematologic condition of an animate subject as recited in claim 26 wherein said conveying is effected using radio frequency communications.

29. An apparatus for measuring at least one hematologic condition of an animate subject as recited in claim 26 wherein said conveying is effected using sonically coupled communications.

30. An apparatus for measuring at least one hematologic condition of an animate subject as recited in claim 26 wherein said conveying is effected using magnetically coupled communications.

31. An apparatus for measuring at least one hematologic condition of an animate subject as recited in claim 26 Wherein said conveying is effected using inductively coupled communications.

32. An apparatus for measuring at least one hematologic condition of an animate subject as recited in claim 26 wherein said conveying is effected using capacitively coupled communications.

33. An apparatus for measuring at least one hematologic condition of an animate subject as recited in claim 24 or 25 wherein the apparatus is arranged with said laser device and said light detection device in an orientation capable of substantially facing the animate subject, said light detection device receiving said resultant light having been reflectively scattered by said animate subject.

34. An apparatus for measuring at least one hematologic condition of an animate subject as recited in claim 24 or 25 wherein the apparatus is arranged with said laser device and said light detection device in a substantially facing orientation; said light detection device receiving said resultant light having been reflectively scattered by said subject.

35. An apparatus for measuring at least one hematologic condition of an animate subject as recited in claim 24 or 25 wherein the apparatus comprises means for monitoring said subject for an extended period of time.

36. An apparatus for measuring at least one hematologic condition of an animate subject as recited in claim 35 wherein the apparatus is configured as a clothing accessory.

37. A method for measuring at least one selected physical condition of an animate subject; the method comprising:
    illuminating said subject by a light source
    receiving resultant light from said subject at a light receiver;
    receiving indication of said resultant light from said light receiver by an information processor connected with at least said light receiver;
    evaluating said indication to effect said measuring, said information processor being implemented in a unitary structure with at least one of said light source and said light detector; said unitary structure comprising;
    a monocrystalline silicon substrate;
    a monocrystalline perovskite oxide material overlying at least a portion of the monocrystalline silicon substrate;
    an amorphous oxide material located between the monocrystalline perovskite oxide material and the monocrystalline silicon substrate; and
    a monocrystalline compound semiconductor material overlying at least a portion of the monocrystalline perovskite oxide material,
    wherein at least a portion of the information processor is formed within the monocrystalline silicon substrate and at least a portion of the light source is formed within the monocrystalline compound semiconductor material.

38. A method for measuring at least one selected physical condition of an animate subject as recited in claim 37, the method further comprising:
    effecting said evaluating in response to a command to provide said indication, wherein said evaluating comprises
        determining a diagnostic sequence for illumination,
        commanding said light source to perform said diagnostic sequence,
        operating said light source to transmit light upon said subject according to said diagnostic sequence,
        receiving resultant light from said subject, and
        analyzing said resultant light; and
    communicating said indication to a remote locus.

39. A method for measuring at least one selected physical condition of an animate subject as recited in claim 37, wherein said evaluating comprises:
    determining a measuring time according to at least one first criterion;
    substantially at the measuring time, determining a diagnostic sequence for illumination;
    commanding said light source to perform the diagnostic sequence; operating said light source to transmit light according to the diagnostic sequence;
    receiving resultant light from said animate subject;
    analyzing the resultant light according to at least one second criterion; and
    when the resultant light satisfies said at least one second criterion, communicating said indication to a remote locus.

* * * * *